United States Patent
Chen et al.

(10) Patent No.: US 7,154,398 B2
(45) Date of Patent: Dec. 26, 2006

(54) WIRELESS COMMUNICATION AND GLOBAL LOCATION ENABLED INTELLIGENT HEALTH MONITORING SYSTEM

(76) Inventors: Thomas C. H. Chen, 5468 Cedar Creek Dr., Houston, TX (US) 77056; Connie J. Chen, 5468 Cedar Creek Dr., Houston, TX (US) 77056

(*) Notice: Subject to any disclaimer, the term of this patent is extended or adjusted under 35 U.S.C. 154(b) by 99 days.

(21) Appl. No.: 10/337,096

(22) Filed: Jan. 6, 2003

(65) Prior Publication Data

US 2004/0130446 A1 Jul. 8, 2004

(51) Int. Cl.
*G08B 23/00* (2006.01)

(52) U.S. Cl. .............................. 340/573.1; 340/573.4; 340/581; 340/582; 340/584; 340/426.18; 340/539.12; 340/539.13; 600/300; 600/301; 600/322; 600/595

(58) Field of Classification Search .............. 340/573.1, 340/573.4, 581, 582, 584, 586, 426.18, 539.12, 340/539.13; 600/300, 301, 322, 595
See application file for complete search history.

(56) References Cited

U.S. PATENT DOCUMENTS

| | | | |
|---|---|---|---|
| 5,479,932 A | 1/1996 | Higgins et al. | |
| 5,749,365 A | 5/1998 | Magill | |
| 5,778,882 A | 7/1998 | Raymond et al. | |
| 5,897,493 A | 4/1999 | Brown | |
| 5,899,855 A | 5/1999 | Brown | |
| 5,960,403 A | 9/1999 | Brown | |
| 6,073,046 A | 6/2000 | Patel et al. | |
| 6,095,985 A | 8/2000 | Raymond et al. | |
| 6,101,478 A | 8/2000 | Brown | |
| 6,144,837 A | 11/2000 | Quy | |
| 6,160,478 A | 12/2000 | Jacobsen et al. | |
| 6,168,563 B1 | 1/2001 | Brown | |
| 6,171,237 B1 | 1/2001 | Avital et al. | |
| 6,282,441 B1 | 8/2001 | Raymond et al. | |
| 6,292,698 B1 * | 9/2001 | Duffin et al. | 607/32 |
| 6,577,893 B1 * | 6/2003 | Besson et al. | 600/509 |
| 6,579,231 B1 * | 6/2003 | Phipps | 600/300 |

* cited by examiner

*Primary Examiner*—Tai T. Nguyyen

(57) ABSTRACT

A wireless communication and global location enabled intelligent health monitoring system comprising of a plurality of wireless medical sensor apparatus that include an active sensor, a transducer, a digital-to analog converter, a frequency synthesis, a plurality of bandpass filter, a plurality of linear power amplifier, a signal mixer, a packaged antenna, a thin-film battery, for measuring patient vital signs on different parts of patient body, and a main processing unit apparatus that contains a system software including intelligent controller which uses active, real-time monitoring method to measure and process vital signs and location information for providing alert on location and transmitting emergency request to remote patient monitoring station for immediate assistance. Intelligent controller and all application tasks of said system software are running under separate parallel execution threads. Under an urgent situation, the two-way wireless communication, global position data and adaptive location assessment capabilities allow an emergency service vehicle to be dispatched to the patient that carries the system. The system includes a (Hypertext Transmission Protocol) HTTP Web server that can respond to a remote request sent wirelessly either from a patient monitoring station or a patient's family member through a standard Internet browser, anywhere and anytime. The system uses a rechargeable/removable battery in conjunction with a software control to recharge the system and conserve system power consumption.

26 Claims, 22 Drawing Sheets

Wireless Medical Sensor Apparatus In Non-Irritated Adhesive Tape Form

Wireless Medical Sensor Apparatus In Adjustable Bracelet Band Form

| | |
|---|---|
| Patient Environment: | Outdoor, Open Field, Clear Sky, Rural Area. |
| Location Assessment: | Primary – Global Position System (GPS) Data<br>Secondary – Cellular Base Station Signal Strength Measurement or Cellular Base Station Time-Of-Arrival Measurement |

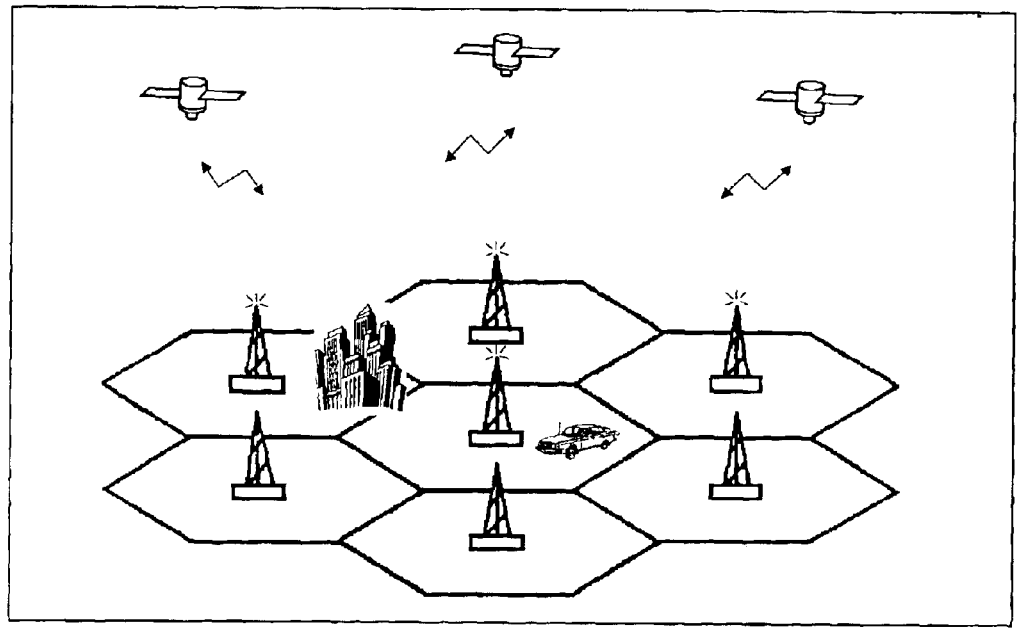

| | |
|---|---|
| Patient Environment: | Under High-Raised Building, At City Downtown, Cloudy Sky, Inside Building, Inside Vehicle, Inside Shopping Mall, During Time-To-First-Fix (TTFF) Period of GPS Data Acquisition. |
| Location Assessment: | Primary – Cellular Base Station Signal Strength Measurement or Cellular Base Station Time-Of-Arrival Measurement<br>Secondary – Global Position System (GPS) Data |

Figure 12

WIRELESS COMMUNICATION AND GLOBAL LOCATION ENABLED INTELLIGENT HEALTH MONITORING SYSTEM

BACKGROUND

1. Field of Invention

This invention relates in general to a health monitoring system, and in particular to the incorporation of two-way wireless communication, global location acquisition and wireless medical sensor into an intelligent health monitoring system for concurrent measuring, processing, alerting and transmission of multiple health-related vital signs of the patient wearing the system.

2. Description of Prior Art

The health monitoring system is well-understood in the art. It can be used to measure a patient's relevant vital parameters, such as blood pressure, glucose concentration, heart rate and body temperature. The measurement can be taken either continuously or at predetermined time, without the need for an in-hospital examination. The system can also be used to alert the patient and to send an emergency request to a local 911 emergency service.

Different vital sign measuring, collection and reporting methods can be used in a health monitoring system. For example, U.S. Pat. No. 6,095,985, U.S. Pat. No. 6,282,441, and U.S. Pat. No. 5,778,882, all by Raymond et al., describe a health monitoring system that collects the patient's vital signs and periodically uploads the data to a remote database where it is stored along with similar health histories for other patients. In another example, U.S. Pat. No. 6,073,046 to Patel et al. reveals a medical facility that collects the signals of a cardiovascular patient and transmits it to a remote location for analysis. Another relevant example is U.S. Pat. No. 6,171,237 to Avitall et al. that explains a remote health monitoring system that receives data from a plurality of remote test unit which is configured for a particular patient for optimal care. The health monitoring systems in the above patents are passive, data collection based systems in which the patient's vital signs are measured and transmitted to a remote location for processing and analysis. An alert, when triggered by the results of data analysis, is then sent back to the health monitoring system or to an emergency service bureau for further action. A preferable alternative to the passive, collection based system is an active, real-time monitoring based system which can measure, process, and analyze a patient's vital signs on location. Whenever an alert regarding patient's vital signs is trigged, an alarm can be activated on location to warn the patient while transmitting the information to a remote emergency service station. An example of such a situation can be pictured as a man who is lifting heavy equipment and subsequently hears a beeping sound from the health monitoring system. The beeping alerts him of an irregularity in his heart beat and warns him to stop working immediately to avoid cardiac arrest. Additional panic button can also be included in such system to be used whenever he/she feels uncomfortable about his/her health condition at anytime. Once the panic button is pressed, all vital sign data can be transmitted to a designated patient monitoring station for immediate attention.

The sensor devices of the health monitoring system are responsible for conducting vital sign measurements. The sensor devices can be located either next to the main processing unit of the health monitor system or at a position remote from patient's body where vital signs are more easily measured. For example, U.S. Pat. No. 5,479,932 to Higgins et al. describes an infant health monitoring system that includes a passive sensor connected next to a microcontroller for detection of gross motor movement, heart rate and respiration rate of the infant. When the sensor device is located at a remote position, cable wire is typically used for network connection and data transfer between the sensor device and the main processing unit. The method of attaching the sensor device next to the main processing unit as mentioned in the patent of Higgins et al. or connecting the sensor device through cable wire is inflexible if multiple sensor devices are needed for different vital sign measurements. This method will also interfere with patient's normal movement sometime. A preferable method is the use of a wireless medical sensor that not only has the capability of conducting vital sign measurement from a specific location on the patient's body but also includes the necessary apparatus to transmit data back to the main processing unit through a short-range Radio Frequency (RF) network. With a wireless medical sensor, the main processing unit of a health monitoring system can either be worn by a patient when he/she is on the move, or placed at a nearby location in the house, office, car, or wherever the short-range RF network can be reached.

The long-range data communication between the health monitoring system and the remote patient monitoring station can be conducted through either a wireline or a wireless communication network. Numerous systems have used wireline communication network as a primary mean for transmission of patient data. For example, U.S. Pat. No. 5,899,855, and U.S. Pat. No. 5,960,403, both to Brown, describe a modular self-care health monitoring system that employs a compact microprocessor-based unit for the operation of a glucose monitor, and the transmission of a signal to a remote clearing house or healthcare facility via telephone lines. Another example, U.S. Pat. No. 5,897,493 and U.S. Pat. No. 6,101,478, both to Brown, discloses a monitoring system for remote query of an individual with remote apparatus connected to a wireline telephone network. In U.S. Pat. No. 6,144,837, Quy describes an electronic health monitoring system for interactively monitoring an individual's physical condition and for providing health-related information to a television set through a television interface cable. Other systems have attempted to use a wireless communication network for conducting limited health monitoring functions. For example, in U.S. Pat. No. 6,160,478, Jacobsen et al. explain a system for remotely monitoring a patient's physical activity by including an accelerometer which is capable of measuring both the magnitude and direction of motion acceleration. The invention from Jacobsen et al, however, is limited to monitoring body acceleration and cannot measure other vital signs. Another example is U.S. Pat. No. 5,749,365 to Magill that explains a method for monitoring vital signs of a human or animal subject. The wireless device invented by Nagill is only cable of one-way data transmission and cannot provide two-way wireless communication. A desirable health monitoring system should include a long-range two-way wireless data communication module that can be used to support active, real-time vital sign monitoring of the patient. The long-range wireless data communication apparatus used in such a system shall be adopted to different cellular networks, such as Global Services for Mobile (GSM), Code Division Multiple Access (CDMA), General Packet Radio Service (GPRS) and Cellular Digital Packet Data (CDPD).

Tracking a patient's whereabouts is very important in a health monitoring system. There are two ways to determine the location of a mobile device worn by a patient: acquiring Global Position System (GPS) data by the mobile device or measuring the distance from the mobile device to nearest Base Station (BS) of the cellular network towers. GPS is a spaced-based navigation and positioning system that allows the location of a receiving system to be determined autonomously. The GPS consists of three major segments: the Space Segment, the Control Segment, and the User Segment. While the Space Segment and Control Segment are operated and administrated by the U.S. Space Command of the U.S. Air Force, the User Segment can exist either as a stand-alone commercially available receiver, or as an integration module that can be embedded into a mobile device. To accurately determine the location of a mobile device, at least three GPS satellites need to be in the line-of-sight by the mobile device. In addition to acquiring GPS data, if a mobile device is equipped with a long-range two-way wireless communication module, a mobile device's location can also be determined either by measuring the strength of a RF signal sent from the Base Stations of nearby cellular network towers, or by measuring the signal's Time-Of-Arrival (TOA) from Base Station to the mobile device. The location of the mobile device is then calculated through triangulation of signal strength or signal TOA from multiple Base Stations. A patient who wears the mobile device may be traveling in and out of different locations, or may stay at one location for a long period of time. Depending on the environment of the location, GPS data and Base Station distance data might not available. A more intelligent method is to detect the environment that the patient is currently in, and to adaptively assess the patient's location based on the last available GPS data and/or Base Station distance. Therefore, a preferable health monitoring system is to include an adaptive location assessment module and method, which allows a patient who wears the system to be located. This preferable health monitoring system also enables an Emergency Service Vehicle to be dispatched to the location of a patient in extreme distress or in an emergency situation.

The expansion of high speed Internet access and its comprehensive capabilities have impacted many ways of people's daily lives in recent years. The Internet and related technologies can be used in a health monitoring system to the patient's advantage. For example, in U.S. Pat. No. 6,168,563, Brown describes a system and a method that enables the health care provider to monitor and manage a health condition of a patient through a communication network such as the World Wide Web (WWW). In this invention, however, the remote health monitoring system worn by a patient is a Web-client based system, not a Web-server based system. A Web-client based health monitoring system can only respond to the request of a remote server, such as sending a patient's vital information back to the server. Such a system is operating in a passive mode and cannot react to an urgent health condition encountered by a patient in real-time when needed. One alternative to the Web-client based health monitoring system is to embed a Hypertext Transmission Protocol (HTTP) Web server in the system. In this way, a preferable health monitoring system can integrate a long-range two-way wireless communication module with a HTTP Web server. This allows the patient's family member and the medical staffs to access the system at a remote patient monitoring station using a standard Internet browser even when the patient is on the move.

A health monitoring system conducts vital sign measurements either individually or concurrently depending on system configuration. To support active, real-time monitoring functions, the system needs to decode signals from a wireless medical sensor, process measured data, and provide alter to patient if needed. In addition, the system needs to respond to external requests regarding the patient's vital signs and location. By including the capability of wireless data transmission in the system, it also needs to handle incoming and outgoing signal through a two-way wireless communication network. To provide adaptive location assessment in the system, the monitoring system also needs to retrieve and process position data from GPS satellites, and to calculate the distance from the multiple Base Station's cellular towers. Furthermore, the system needs to perform battery conservation related functions, such as putting application tasks into sleeping mode, and wake application tasks up at a pre-determined time. To administrate and manage all the above mentioned tasks simultaneously, the preferred health monitoring system should be capable of concurrent processing. In such a system, a plurality of task shared memory are created and used by all application tasks to post related task data, and receive processing instructions from an intelligent controller. An intelligent controller is responding for starting and stopping of all application tasks using the information at the task shared memory. The execution of the intelligent controller and all other application tasks are running under separate system threads concurrently to fully utilize the system's processing power.

In a mobile and wireless based health monitoring system, conserving electronically power is an important concern. The method of power conservation in such a system is to consume the least power when conducting all application tasks, and allows the system to be running for long periods of time without needing to change the power source. The preferred method of conserving power in a health monitor system is to monitor power usage through software control. In such a method, application tasks are put in sleep mode when not needed and woken up when system condition has changed or at a pre-determined time. In addition, removable and rechargeable battery is used in such a system to allow power source to be charged easily and frequently.

A need exists for a health monitoring system that uses an active, real-time monitoring method to measure and process a patient's vital signs for providing an alert on location and sending emergency requests to a remote patient monitoring station for immediate action. A need exists for a health monitoring system that contains a wireless medical sensor not only for measuring a patient's vital signs, but also for transmitting measured data to the main processing unit through short-range RF network. A need exists for a health monitoring system that incorporates the capabilities of a long-range two-way wireless communication module and a Global Position System (GPS) module along with an adaptive location assessment method for determining a patient's location. This data can then be used to transmit location information wirelessly to an Emergency Service Vehicle or a remote patient monitoring center. A need exists for a health monitoring system including a HTTP Web server that can respond to remote requests either from a patient monitoring station or from a patient's family member using a standard Internet browser, anywhere and anytime. A need exists for a health monitoring system that includes task shared memory and an intelligent controller to administrate and manage all related application tasks running concurrently under separate parallel execution threads. A need exists for a health monitoring system that uses a removable and rechargeable battery in conjunction with a software control to recharge the system and control the system's power consumption.

OBJECTS AND ADVANTAGES

It is therefore an object of the invention to provide a health monitoring system that uses an active, real-time monitoring method to measure and process a patient's vital signs. Whenever an irregular health condition is sensed, the system will alert the patient that wears the system to attend to the situation immediately. The system can also transmit an emergency or urgent message autonomously to a remote patient monitoring station for further assistance. The system also includes a panic button, which can be pressed by the patient whenever he/she feels uncomfortable about his/her health status/situation. Once the panic button is pressed, the patient's vital signs data and location information will be transmitted to a designated station.

Another object of this invention is to provide a health monitoring system that contains a plurality of wireless medical sensor which can retrieve vital sign measurements from a specific part of a patient's body and transmit the measured data back to the main processing unit of the health monitor system through a short-range Radio Frequency (RF) network. The main processing unit of the health monitoring system, separate from the wireless medical sensors, can be worn by a patient when he/she is on the move or place in the house, office, car or wherever a short-rang RF network can be reached.

Another object of the invention is to provide a health monitoring system that contains a long-range two-way wireless communication module for maintaining two-way wireless communication between the system and a remote patient monitoring station or a patient's family member. This capability is essential for maintaining an active, real-time monitoring method if the patient is moving around all the time. The long-range two-way wireless communication module contained in the system shall be able to operate in different long-range wireless cellular networks, such as GSM, CDMA, GPRS and CDPD.

Another object of the invention is to provide a health monitoring system that contains a Global Position System (GPS) module for acquiring global positioning data in real-time. As part of this object, the health monitoring system uses an adaptive location assessment method that filters and assesses a patient's location based on the availability and accuracy of GPS data and Base Station distance. The application server at a remote location can then request the location data in order to track a patient's whereabouts. The location data can also be transmitted, through a long-range cellular network, to a local E-911 center so that an Emergency Service Vehicle (ESV) can be dispatched to the patient.

Another object of the invention is to provide a health monitoring system that has a HTTP Web server embedded into the system. By integrating a HHTP Web Server with a long-range two-way wireless communication module, the patient's vital signs and location information can be accessed by family members or medical staff at patient monitoring station. They can retrieve this information through a standard Internet browser, anytime and anywhere, while the patient is on the move.

Another object of the invention is to provide a health monitoring system that includes an intelligent control and a plurality of task shared memory to administrate and manage all related application tasks simultaneously. An intelligent controller is responsible for starting and stopping all related application tasks by using the information stored in the task shared memory. The intelligent controller is also responsible for installing new application tasks and uninstalling existing application tasks at runtime, if needed. The execution of the intelligent controller and all other related application tasks are running under separate parallel execution threads concurrently to fully utilize system's processing power.

Another object of the invention is to provide a health monitoring system that uses a removable and rechargeable battery in conjunction with a software control to recharge and conserve the system's power consumption. Software control is carried out by putting application tasks in sleep mode when not needed, and waking them up at proper times when needed. In addition, a removable and rechargeable battery allow power source to be changed easily and frequently. With a special design, this type of battery can be snapped on and off of the health monitoring system, recharged at nighttime, and ready for use next day.

Further objects and advantages of this invention will become apparent from a consideration of the ensuing descriptions and accompanying drawings.

BRIEF DESCRIPTION OF THE DRAWINGS

For a further understanding of the objects and advantages of the present invention, references should be made to the following drawings in conjunction with the accompanying descriptions, wherein:

FIG. 12 is an illustrative schematic diagram the Adaptive Location Assessment Method in an indoor environment in this invention;

Figure 1:
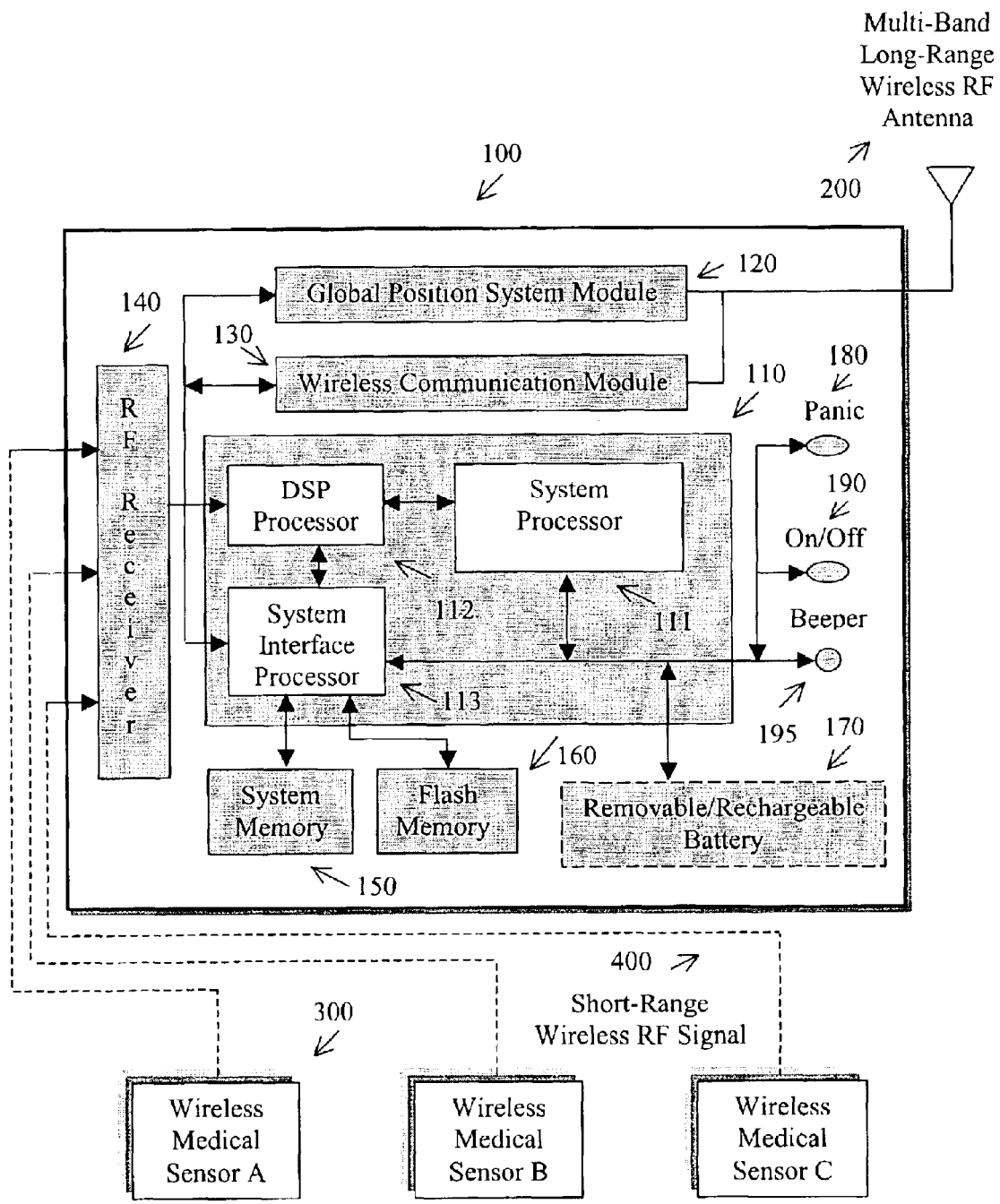
FIG. 1 is an illustrative block diagram of the Main Processing Unit Apparatus of the Wireless Communication and Global Location Enabled Intelligent Health Monitoring System in this invention.

REFERENCE NUMERALS process a patient's vital signs and location information for providing an alert on location and transmitting an emergency request to a remote patient monitoring station for immediate assistance. The key component of Main Processing Unit Apparatus is Main Microcontroller which is connected to Global Position System Module, Long-Range Two-Way Wireless Communication Module, Short-Range RF Receiver, System Main Memory, Flash Memory, Panic Button, On/Off Button, Alert Beeper and Removable/Rechargeable Battery. Main Microcontroller comprises System Processor, Digital Signal Processing (DSP) Processor and System Interface Processor. Both Global Position System Module and Long-Range Two-Way Wireless Communication Module are connected to Multi-Band Antenna, and System Interface Processor, and means for conducting two-way wireless communication and GPS data acquisition simultaneously. Short-Range RF Receiver is connected to DSP Processor, and means for receiving wireless signal from a plurality of Wireless Medical Sensor Apparatus. Wireless Medical Sensor Apparatus comprises the circuitry for both vital sign measurements and short-range RF transmission, and means for measuring and interpreting a patient's vital signs, modulating and transmitting wireless signal back to Short-Range RF Receiver through a short-range RF network.

System Software of the Wireless Communication and Global Location Enabled Intelligent Health Monitoring System resides in System Processor and includes Intelligent Controller, which comprises Task Control Administrator, and a plurality of Task Shared Memory. Task Control Administrator manages and controls the execution of Two-

| | | | |
|---|---|---|---|
| 100 | Main Processing Unit Apparatus | 110 | Main Microcontroller |
| 111 | System Processor | 112 | Digital Signal Processing (DSP) Processor |
| 113 | System Interface Processor | 120 | Global Position System Module |
| 130 | Long-Range Two-Way Wireless Communication Module | 140 | Short-Range Radio Frequency (RF) Receiver |
| 141 | Bandpass Filter | 142 | Amplifier |
| 143 | Signal Mixer | 144 | Bandpass Filer |
| 145 | Amplifier | 146 | Analog/Digital (A/D) Converter |
| 147 | Frequency Synthesizer | 148 | Package Antenna |
| 150 | System Main Memory | 160 | Flush Memory |
| 170 | Removable/Rechargeable Battery | 180 | Panic Button |
| 190 | On/Off Button | 195 | Alert Beeper |
| 200 | Multi-Band Long-Range Wireless RF Antenna | 300 | Wireless Medical Sensor Apparatus |
| 301 | Active Sensor | 302 | Transducer |
| 303 | Digital/Analog (D/A) Converter | 304 | Bandpass Filter |
| 305 | Amplifier | 306 | Signal Mixer |
| 307 | Bandpass Filter | 308 | Amplifier |
| 309 | Frequency Synthesizer | 310 | Packaged Antenna |
| 311 | Thin-Film Battery | 400 | Short-Range Wireless Signal |
| 500 | System Software | 505 | Real-Time Operation System (RTOS) |
| 510 | Intelligent Controller | 511 | Task Control Administrator |
| 512 | Task Shared Memory | 520 | Global Position Data Acquisition Task |
| 521 | Two-Way Wireless Communication Task | 522 | Panic Button Task |
| 523 | HTTP Request Processing Task | 524 | Patient Vital Sign Processing Task |
| 525 | Adaptive Location Assessment Task | 526 | On/Off Button Task |
| 527 | Alert Beeper Activation Task | 528 | Battery Management Task |
| 529 | Wireless Medical Sensor Decoding Task | | |

SUMMARY

A Wireless Communication and Global Location Enabled Intelligent Health Monitoring System comprising of a plurality of Wireless Medical Sensor Apparatus for measuring a patient's vital signs on different parts of a patient's body, and a Main Processing Unit Apparatus containing System Software that uses an active, real-time monitoring method to Way Wireless Communication Task, Global Position Data Acquisition Task, Panic Button Task, HTTP Request Processing Task, Patient Vital Sign Processing Task, Adaptive Location Assessment Task, On/Off Button Task, Alert Beeper Activation Task, Battery Management Task, and Wireless Medical Sensor Decoding Task. All application tasks of System Software are running under separate parallel execution threads. Under an urgent situation, the two-way wireless communication, global position data and adaptive location assessment capabilities allow an Emergency Service Vehicle to be dispatched to the patient that carries the system. The system also includes a HTTP Web server that can respond to a remote request sent wirelessly either from a patient monitoring station or a patient's family member through a standard Internet browser, anywhere and anytime. The system uses a rechargeable/removable battery in conjunction with a software control to recharge the system and conserve system's power consumption.

Preferred Embodiment

Description

FIG. 1 shows the components of Main Processing Unit Apparatus 100 of the Wireless Communication and Global Location Enabled Intelligent Health Monitoring System in this invention. Main Processing Units Apparatus 100 contains System Software 500 which uses an active, real-time monitoring method to measure and process a patient's vital signs for providing an alert on location or sending an emergency request to a remote patient monitoring station for immediate assistance. The key component of Main Processing Unit Apparatus 100 is Main Microcontroller 110 which is connected to Global Position System (GPS) Module 120, Long-Range Two-Way Wireless Communication Module 130, Short-Range Radio Frequency (RF) Receiver 140, System Main Memory 150, Flash Memory 160, Panic Button 180, On/Off Button 190, Alert Beeper 195 and Removable/Rechargeable Battery 170. Main Microcontroller 110 comprises System Processor 111, Digital Signal Processing (DSP) Processor 112, and System Interface Processor 113. Both Global Position System Module 120 and Long-Range Two-Way Wireless Communication Module 130 are connected to Multi-Band Long-Range Wireless RF Antenna 200, and System Interface Processor 113, and means for conducting two-way wireless communication and GPS data acquisition simultaneously. Short-Range RF Receiver 140 is connected to DSP Processor 112, and means for receiving wireless signal from a plurality of Wireless Medical Sensor Apparatus 300. Wireless Medical Sensor Apparatus 300 comprises the circuitry for both vital sign measurements and short-range RF transmission, and means for measuring and interpreting patient's vital signs, modulating and transmitting measured information back to Short-Range RF Receiver 140 through a short-range RF network.

Figure 2:
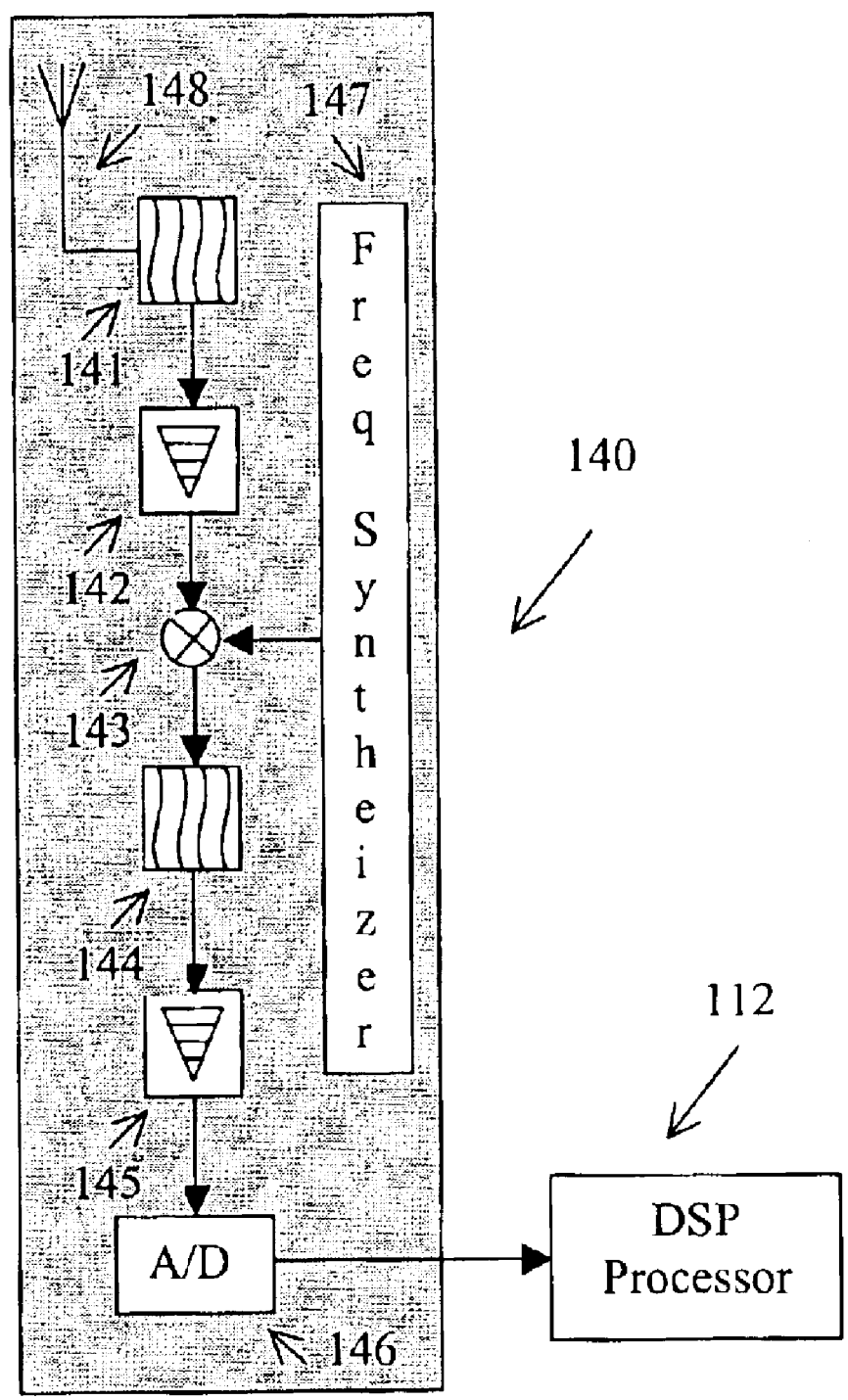
FIG. 2 is an illustrative block diagram of the Short-Range RF Receiver of the Wireless Communication and Global Location Enabled Intelligent Health Monitoring System in this invention.

FIG. 2 shows the components of Short-Range RF Receiver 140 which is connected to DSP Processor 112. Short-Range RF Receiver 140 comprises a Packaged Antenna 148, Bandpass Filter 141, Linear Power Amplifier 142, Signal Mixer 143, Bandpass Filter 144, Linear Power Amplifier 145, Frequency Synthesizer 147, and A/D Converter 146. Short-Range RF Receiver 140 is a spread spectrum based RF receiver, which is implemented in frequency hopping or direct sequence method.

Figure 3:
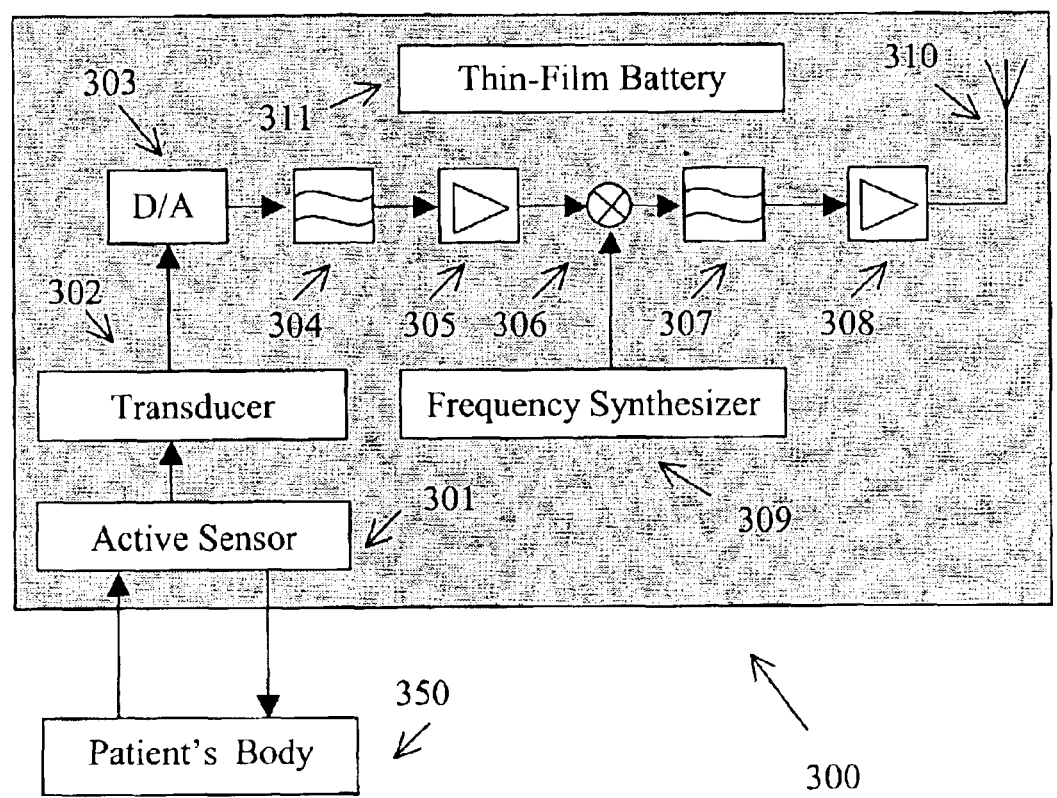
FIG. 3 is an illustrative block diagram of the Wireless Medical Sensor Apparatus of the Wireless Communication and Global Location Enabled Intelligent Health Monitoring System in this invention.
Figure 4:
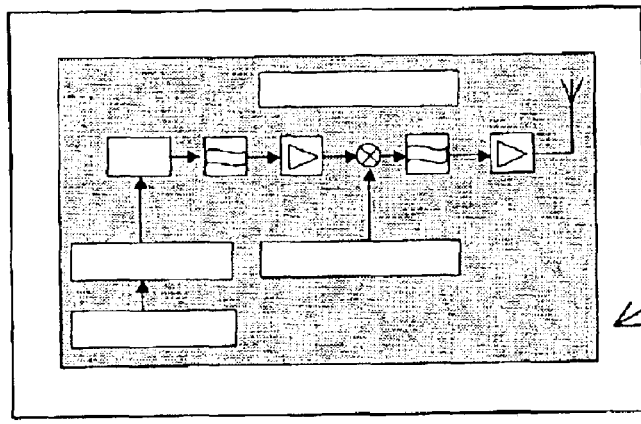
FIG. 4 is an illustrative block diagram of the Non-Irritated Adhesive Tape Implementation of the Wireless Medical Sensor Apparatus in this invention.
Figure 5:
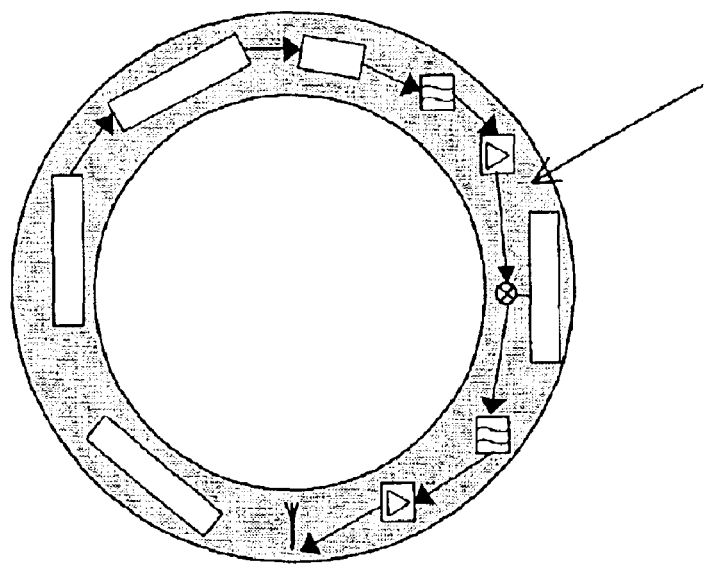
FIG. 5 is an illustrative block diagram of the Adjustable Bracelet Band Implementation of the Wireless Medical Sensor Apparatus in this invention.

FIG. 3 shows the components of Wireless Medical Sensor Apparatus 300 which comprise a thin-film battery 311, and two other sets of circuitry, one for vital sign measurement, and one for wireless signal transmitter. The vital sign measurement portion of the circuitry has direct contact with the patient's body, and comprise of Active Sensor 301 and Transducer 302. The wireless signal transmitter portion of the circuit is connected to the output of Transducer 302, and comprises D/A Convert 303, Bandpass Filter 304, Linear Power Amplifier 305, Signal Mixer 306, Frequency Synthesizer 309, Bandpass Filter 307, Linear Power Amplifier 308, and Packaged Antenna 310. The wireless signal transmitter uses a spread spectrum method to transmit wireless signal to Packaged Antenna 148 of Short-Range RF Receiver 140. FIG. 4 shows the implementation of Wireless Medical Sensor Apparatus 300 in the form of a non-irritated adhesive tape. FIG. 5 shows the implementation of Wireless Medical Sensor Apparatus 300 in the form of an adjustable bracelet band.

Figure 6:
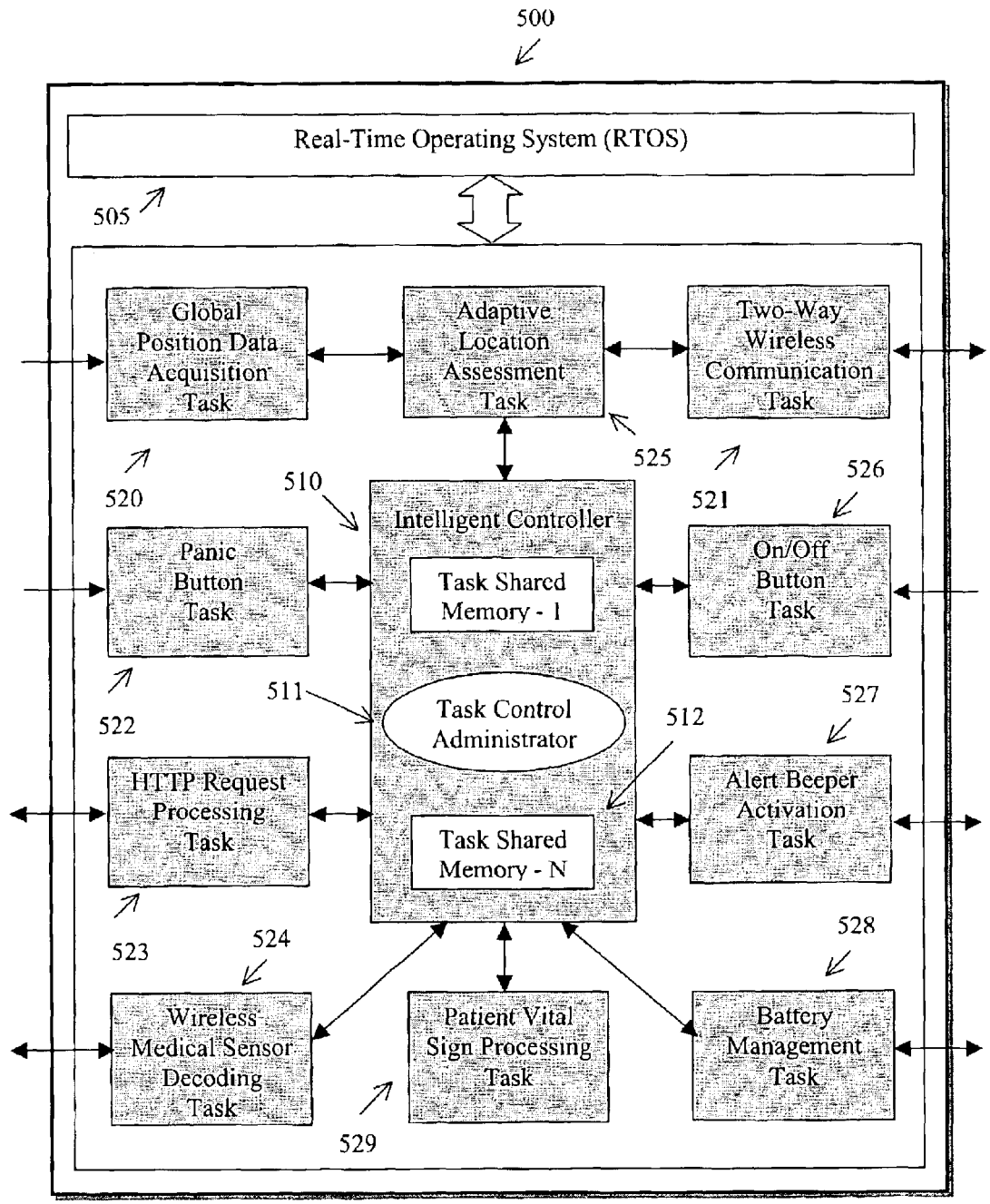
FIG. 6 is an illustrative block diagram of the System Software of the Wireless Communication and Global Location Enabled Intelligent Health Monitoring System in this invention.

FIG. 6 shows the components of System Software 500 of the Wireless Communication and Global Location Enabled Intelligent Health Monitoring System in the invention. Application Tasks of System Software resides in System Processor 111, and includes Intelligent Controller 510 which comprises Task Control Administrator 511, and a plurality of Task Shared Memory 512. Task Control Administrator 511 manages and controls the execution of application tasks which include Global Position Data Acquisition Task 520, Two-Way Wireless Communication Task 521, Adaptive Location Assessment Task 525, Panic Button Task 522, HTTP Request Processing Task 523, Wireless Medical Sensor Decoding Task 524, On/Off Button Task 526, Alert Beeper Activation Task 527, Battery Management Task 528, and Patient Vital Sign Processing Task 529.

Figure 11:
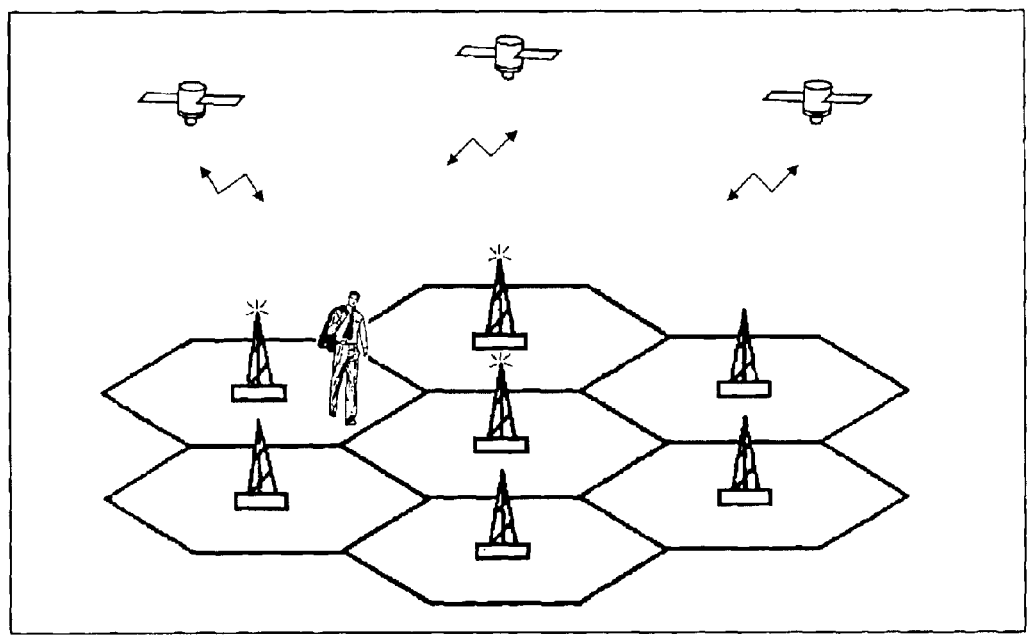
FIG. 11 is an illustrative schematic diagram of the Adaptive Location Assessment Method in an open field environment in this invention.
Figure 13:
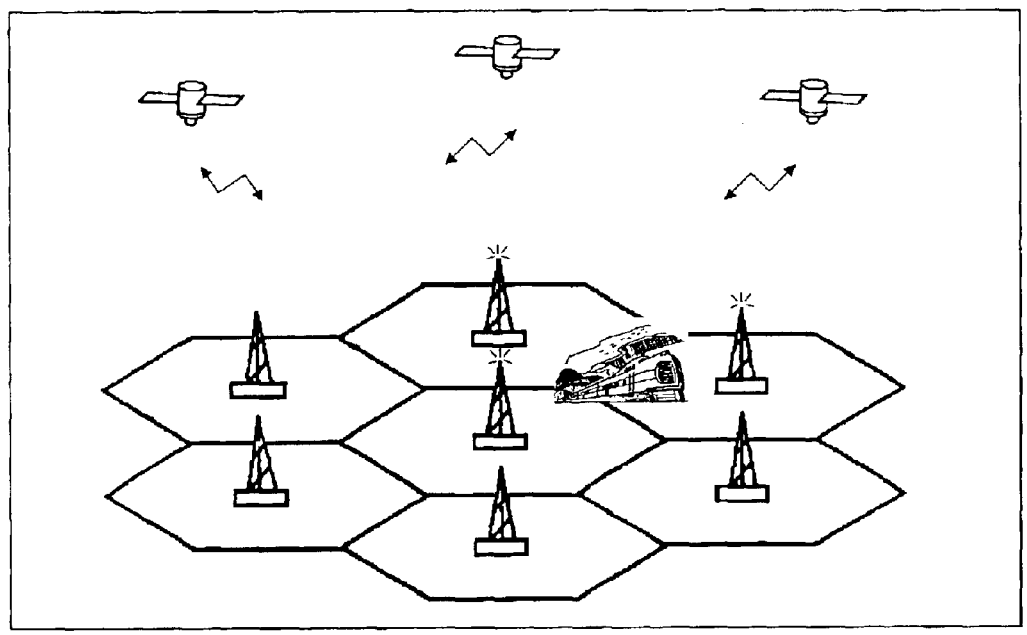
FIG. 13 is an illustrative schematic diagram the Adaptive Location Assessment Method in a wireless signal un-accessible environment in this invention.

FIG. 11 through FIG. 13 are illustrative diagrams of the location source accuracy used by the adaptive location assessment method in this invention. When a patient who wears the Wireless Communication and Global Location Enabled Intelligent Health Monitoring System in this invention is outdoors, in an open field, under clear sky, or in a rural area, the GPS satellites are at the line-of-sight of Main Processing Unit Apparatus 100, and should provide more accurate location data than the Base Station distance data. In this case, GPS data is the primary location source for the adaptive location assessment method, and the Base Station distance is the secondary location source for calculation compensation. When a patient is near a high-rise building, in a city's downtown, under cloudy skies, inside building, inside vehicle, inside shopping mall, or within Time-To-First-Fix (TTFF) period of GPS, the GPS data is temporary not available; hence the Base Station distance is the primary location source. Base Station distance is calculated through triangulation using either signal strength or signal Time-Of-Arrival (TOA) from Base Stations near Main Processing Unit Apparatus 100. When a patient is under a special environment, such as inside tunnel, at basement, or inside elevator, both GPS data and Base Station distance data are not available, an inferred calculation using previous stored GPS data and Base Station distance data derives the best guess location of the patient.

Preferred Embodiment

Operation

Figure 7:
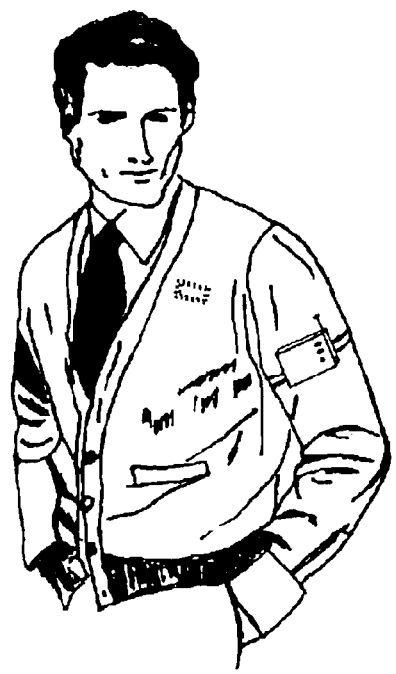
FIG. 7 is an illustrative diagram of the Main Processing Unit Apparatus worn at a patient's arm and the Wireless Medical Sensor Apparatus in Non-Irritated Adhesive Tape form worn at the patient's chest.
Figure 8:
FIG. 8 is an illustrative diagram of the Main Processing Unit Apparatus worn in a patient's pocket and the Wireless Medical Sensor Apparatus in Non-Irritated Adhesive Tape form worn at the patient's chest.
Figure 9:
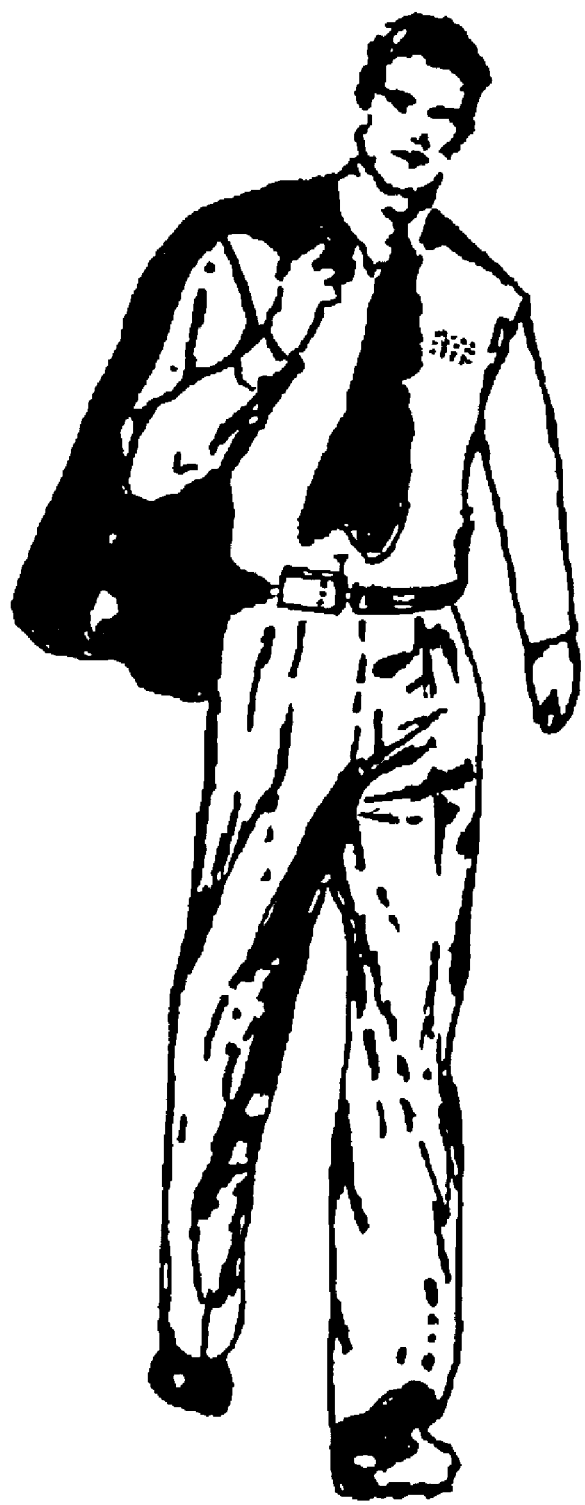
FIG. 9 is an illustrative diagram of the Main Processing Unit Apparatus worn at a patient's waist and the Wireless Medical Sensor Apparatus in Non-Irritated Adhesive Tape form worn at the patient's chest.

Main Processing Unit Apparatus 100 and Wireless Medical Sensor Apparatus 300 in this invention can be worn on different parts of the patient's body. FIG. 7 is an illustrative diagram of Main Processing Unit Apparatus 100 worn on the patient's arm and Wireless Medical Sensor Apparatus 300 worn on the patient's chest. FIG. 8 is an illustrative diagram of Main Processing Unit Apparatus 100 placed inside the patient's pocket and Wireless Medical Sensor Apparatus 300 worn on the patient's chest position. FIG. 9 is an illustrative diagram of Main Processing Unit Apparatus 100 worn at a patient's waist and Wireless Medical Sensor Apparatus 300 worn at the patient's chest.

Figure 10:
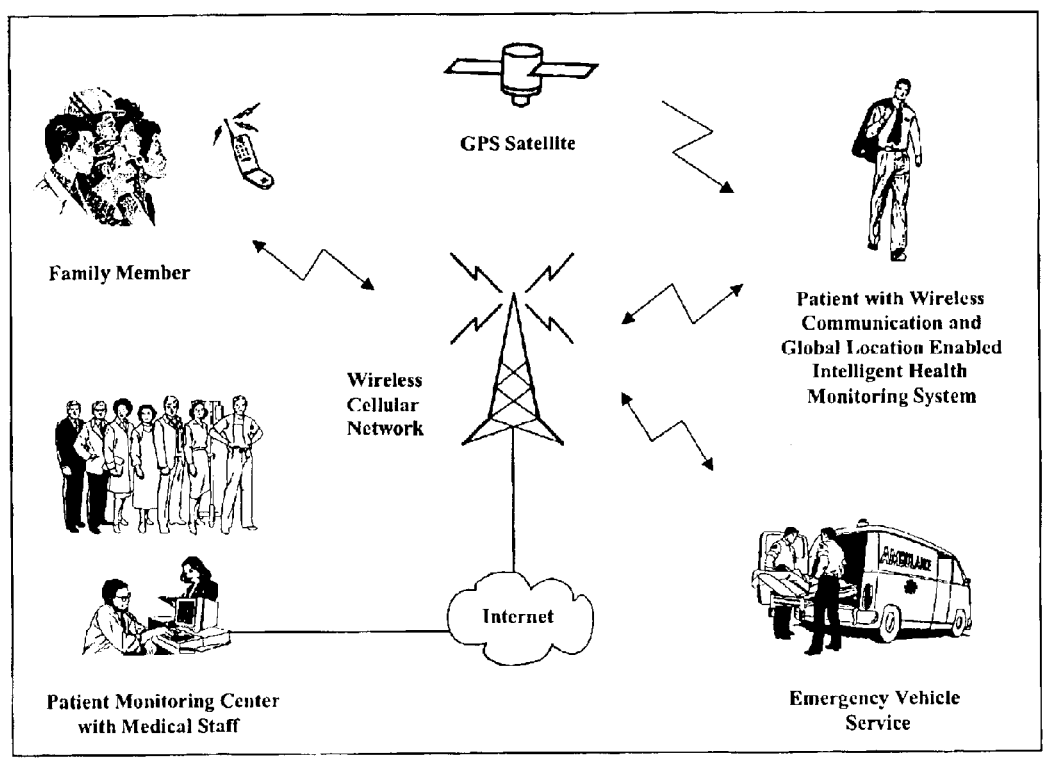
FIG. 10 is an illustrative schematic diagram of the Wireless Communication and Global Location Enabled Intelligent Health Monitoring System in this invention interfacing with other communication systems and interested parties, when both the Main Processing Unit Apparatus and Wireless Medical Sensor Apparatus are worn by the patient.

FIG. 10 is an illustrative schematic diagram that shows the network interface between the Wireless Communication and Global Location Enabled Intelligent Health Monitoring System in this invention and other communication systems. It also shows the operation interaction between the system and other users who are interested in obtaining the patient's vital signs and location information.

Figure 14:
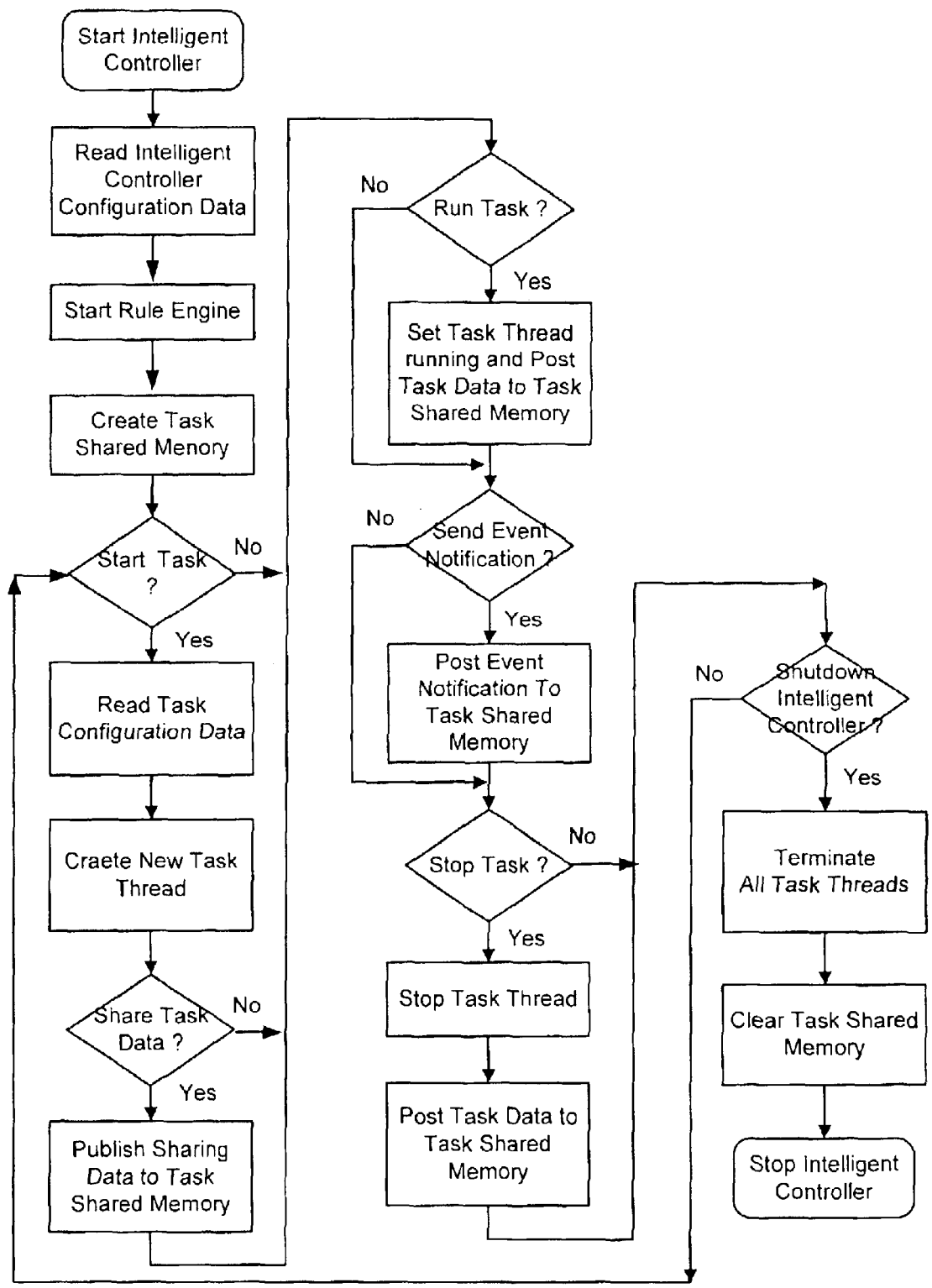
FIG. 14 is a flow chart illustrating the administration and management process flow of the Intelligent Controller in this invention.
Figure 15:
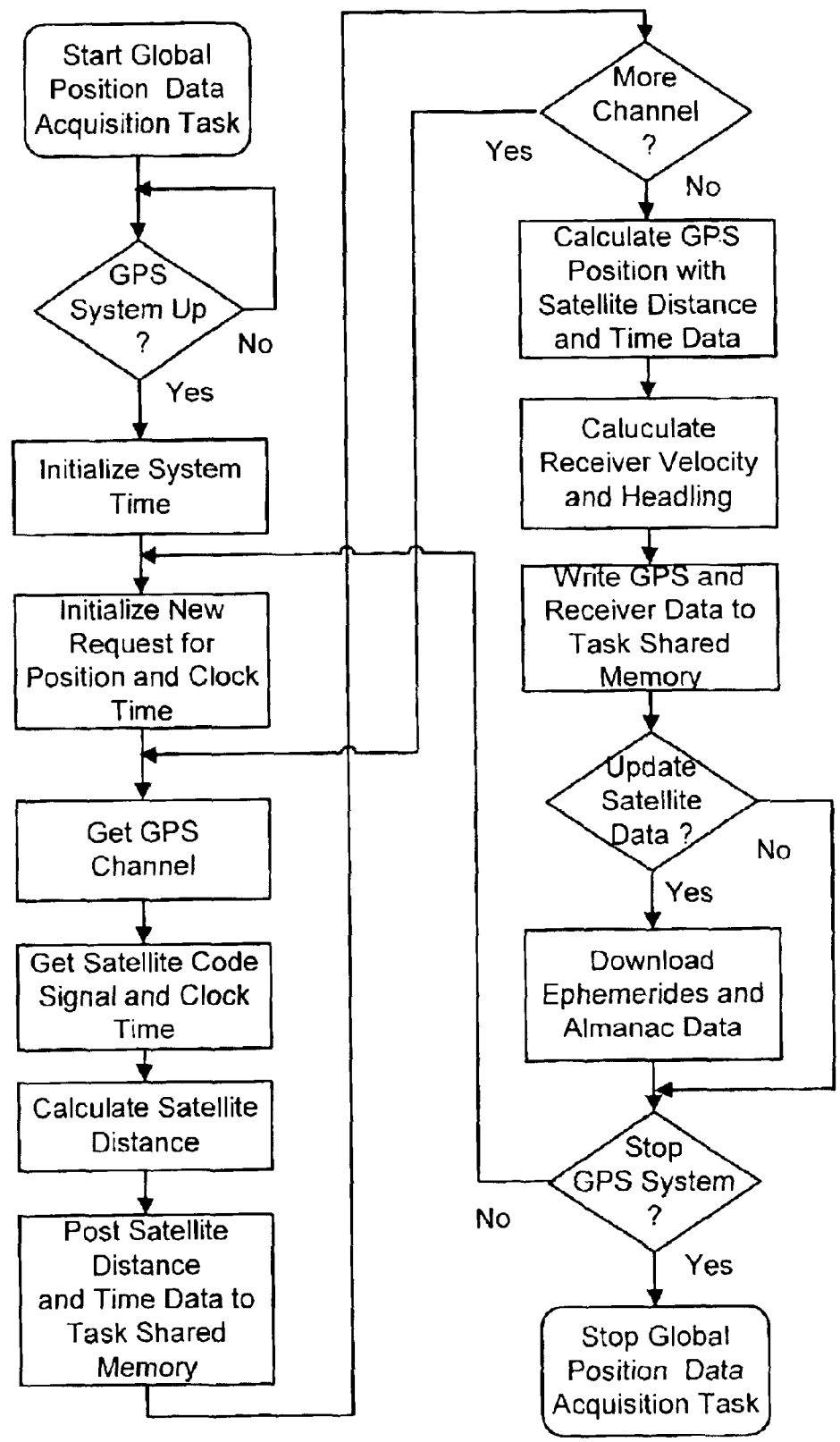
FIG. 15 is a flow chart illustrating the process flow of the Global Position Data Acquisition Task in this invention.
Figure 16:
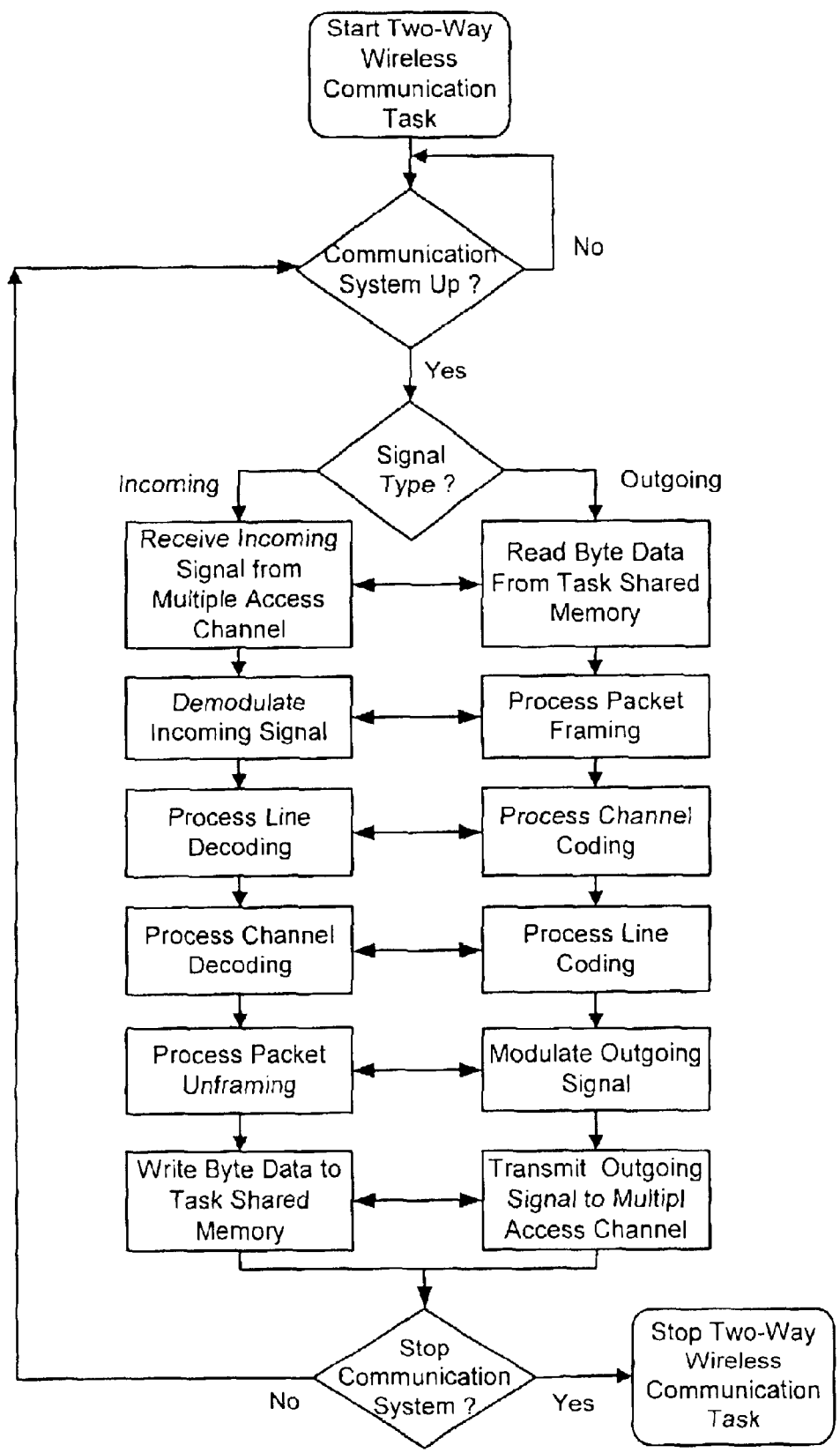
FIG. 16 is a flow chart illustrating the process flow of the Long-Range Two-Way Wireless Communication Task in this invention.
Figure 17:
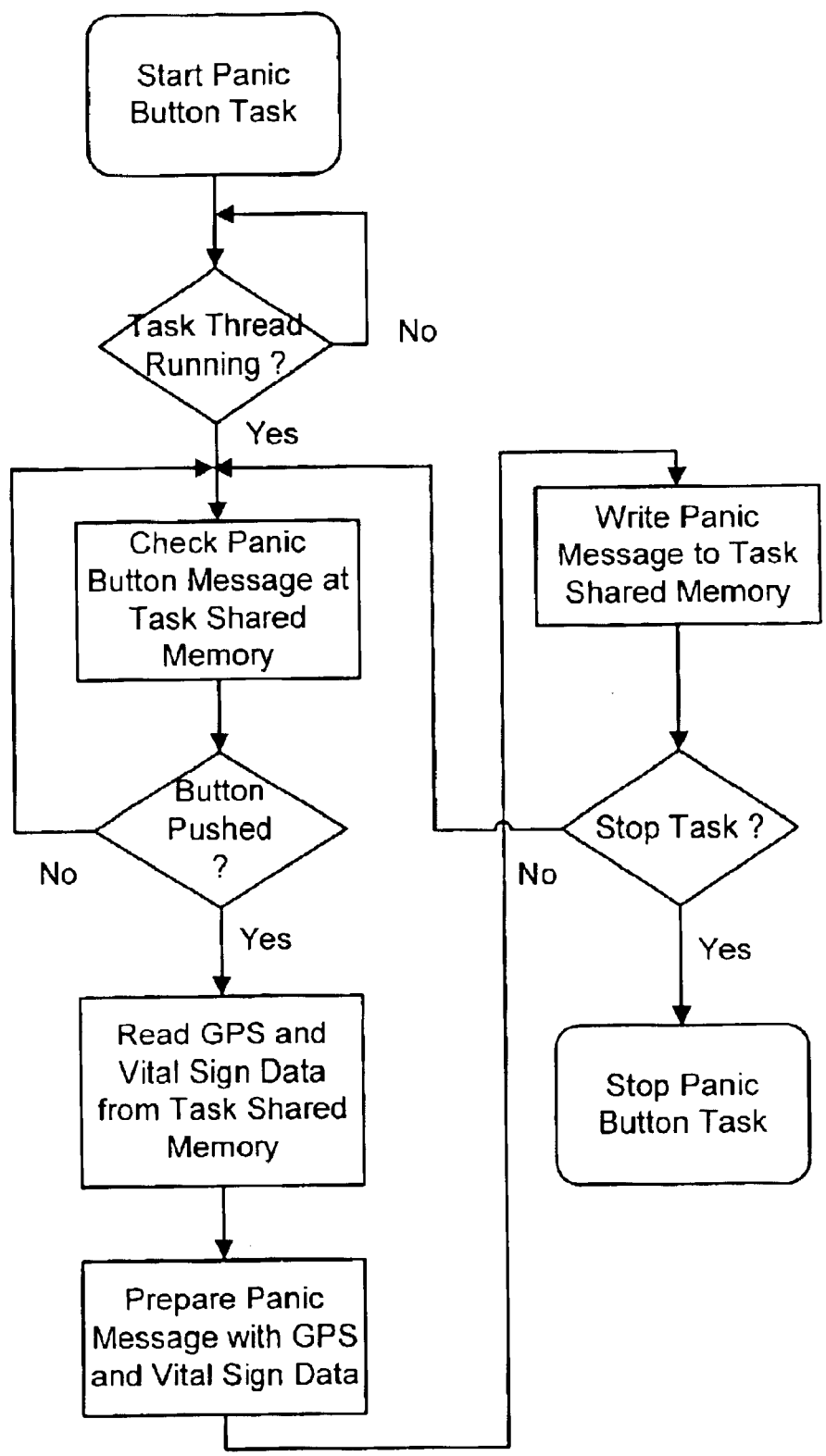
FIG. 17 is a flow chart illustrating the process flow of Panic Button Task in this invention.
Figure 18:
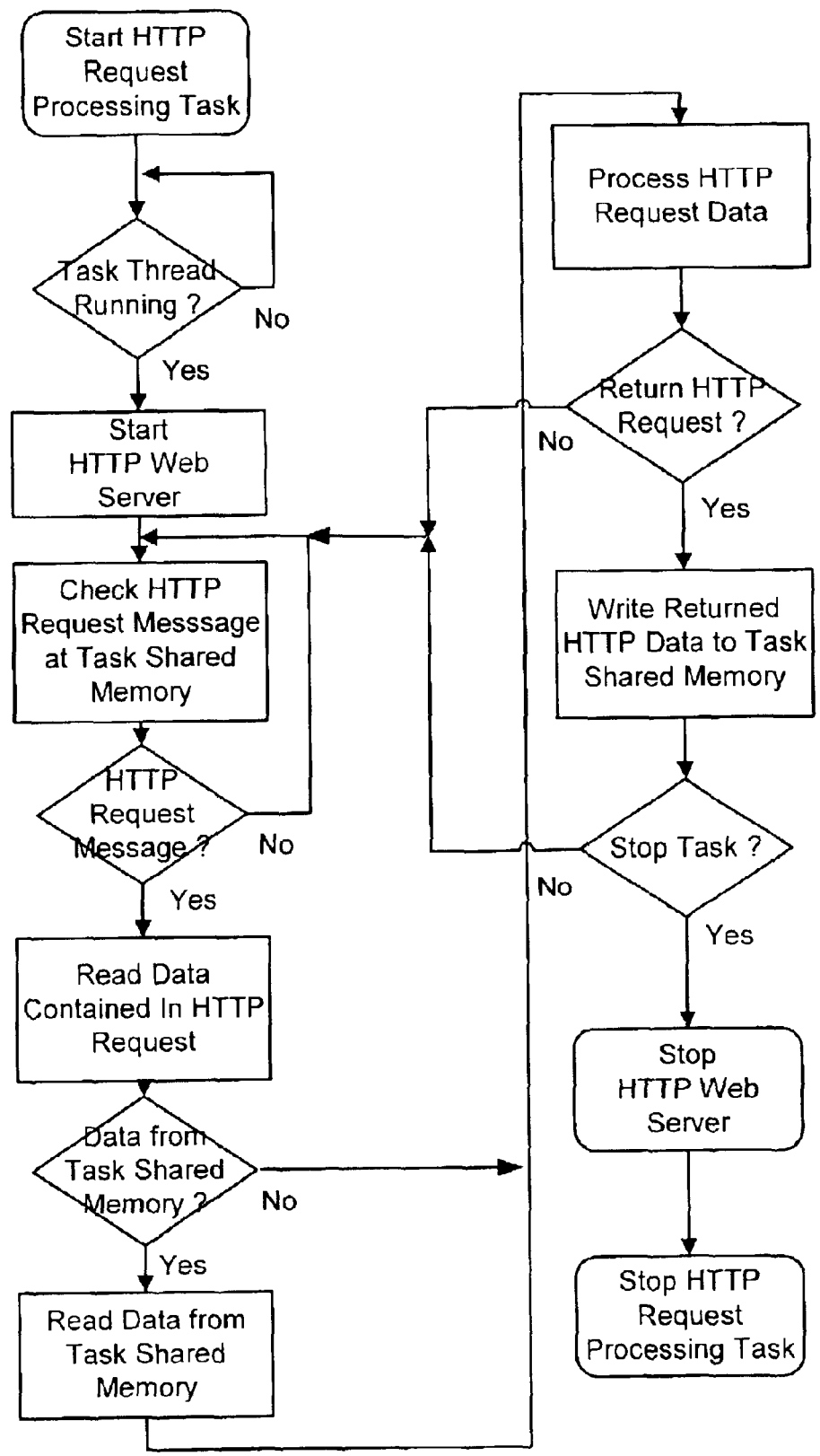
FIG. 18 is a flow chart illustrating the process flow of the HTTP Request Processing Task in this invention.
Figure 19:
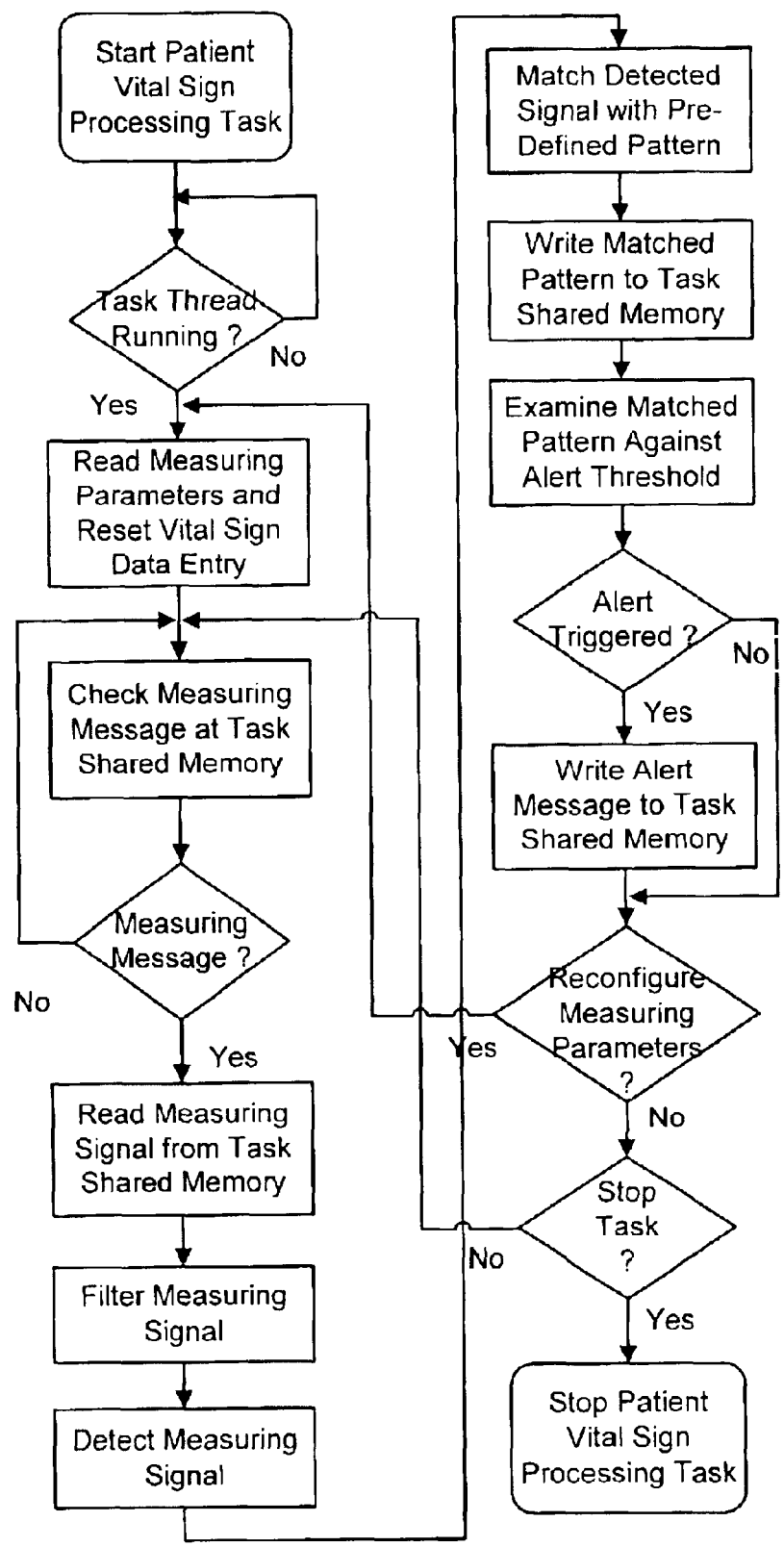
FIG. 19 is a flow chart illustrating the process flow of the Patient Vital Sign Processing Task in this invention.
Figure 20:
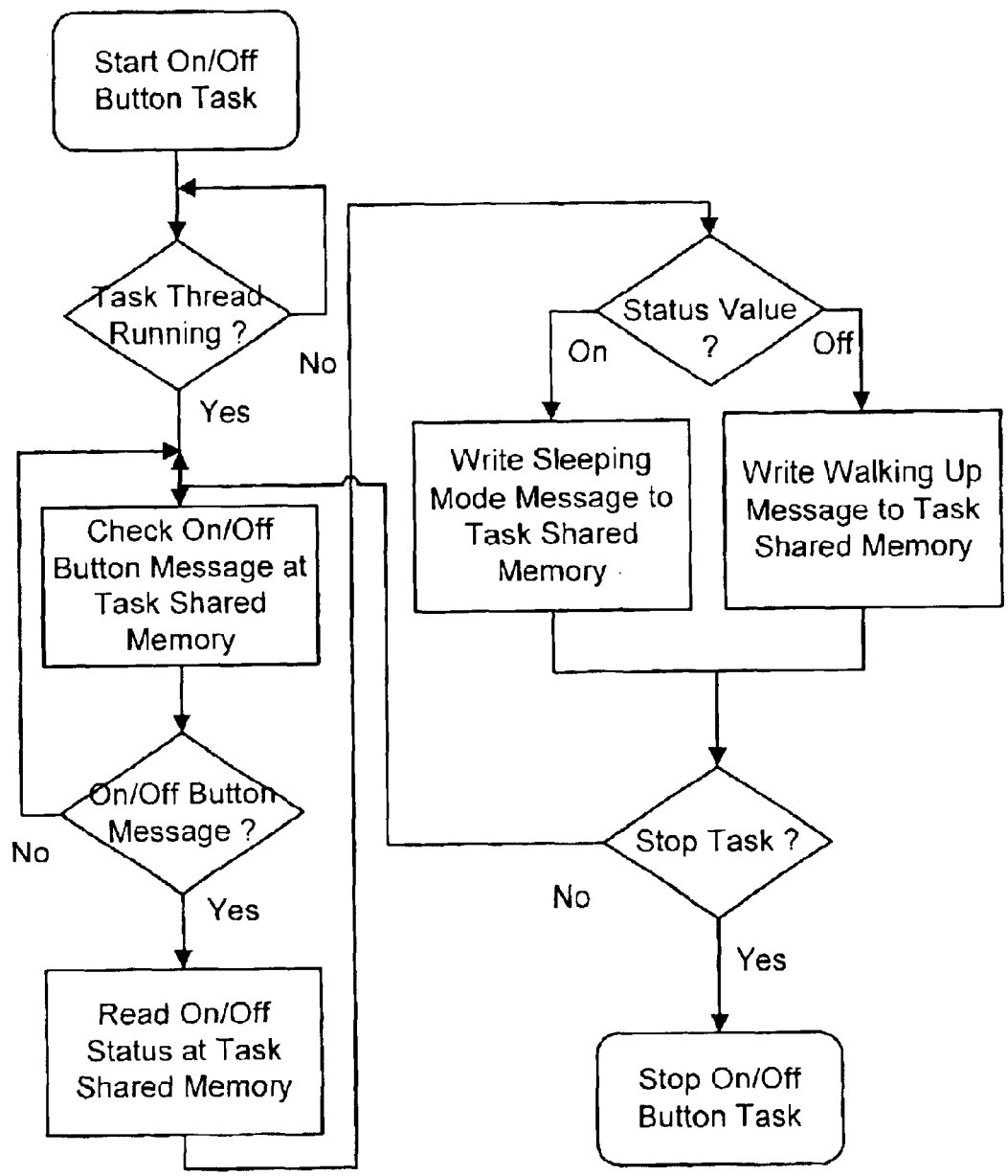
FIG. 20 is a flow chart illustrating the process flow of the On/Off Button Task in this invention.
Figure 21:
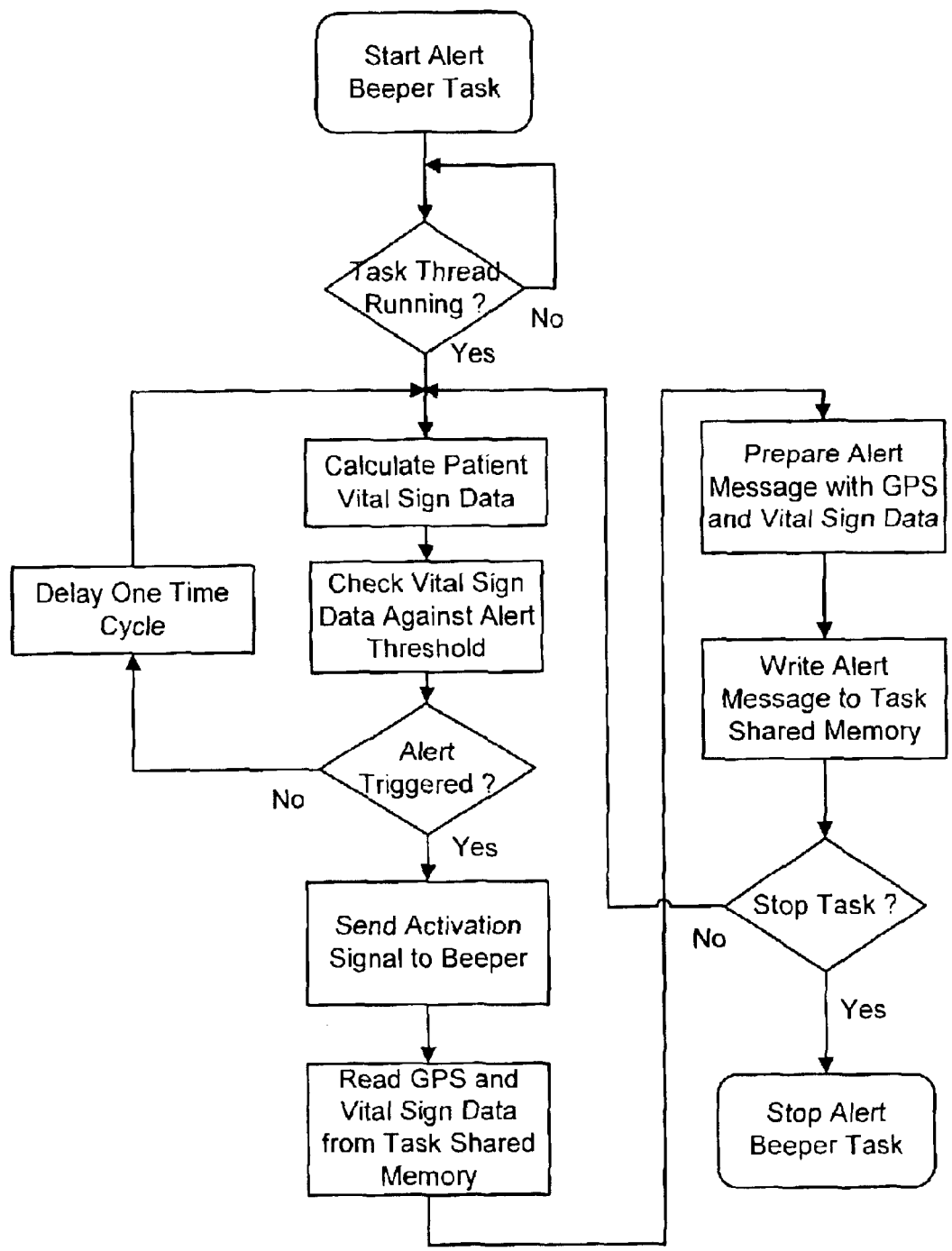
FIG. 21 is a flow chart illustrating the process flow of the Alert Beeper Activation Task in this invention.
Figure 22:
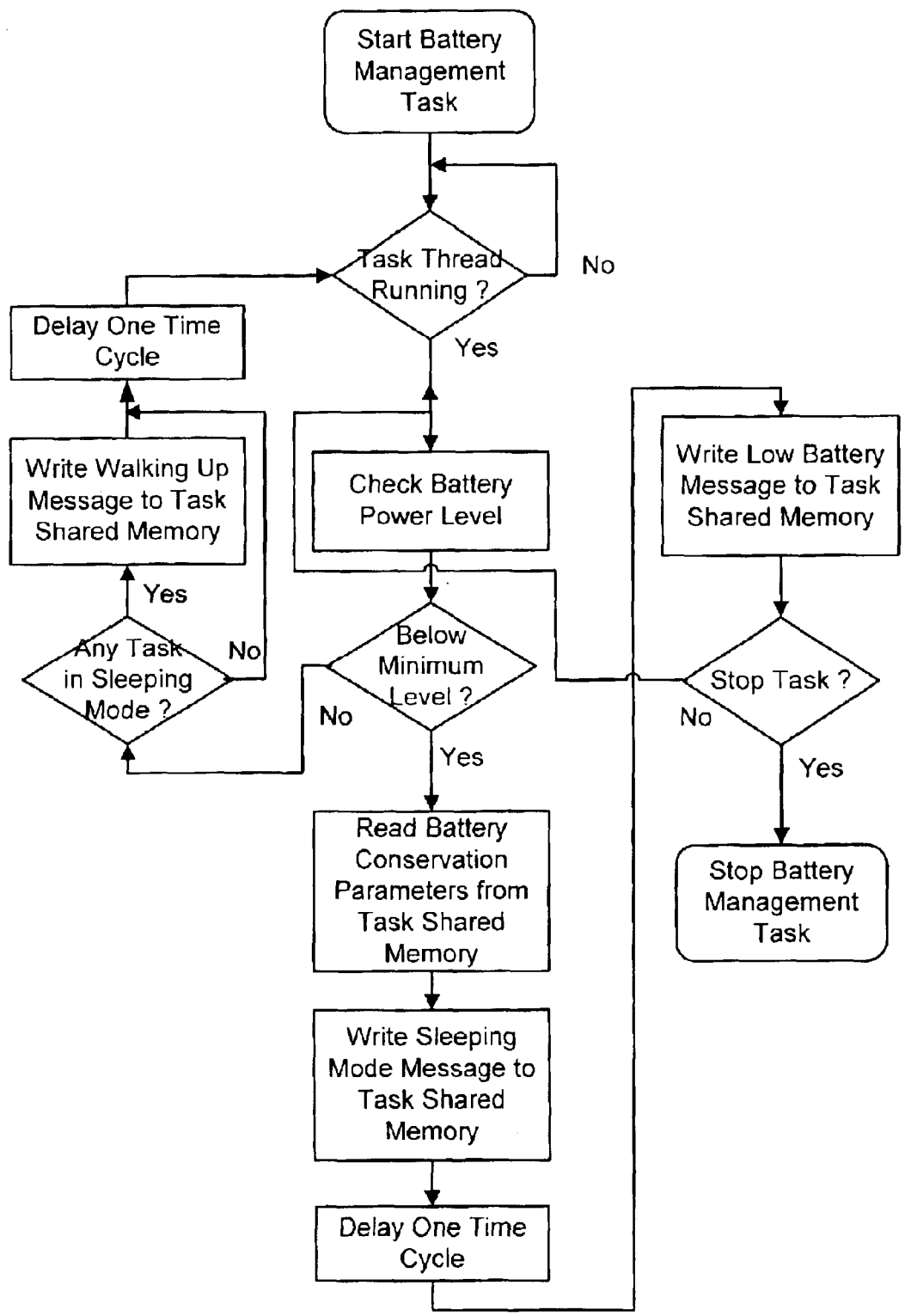
FIG. 22 is a flow chart illustrating the process flow of the Battery Management Task in this invention.
Figure 23:
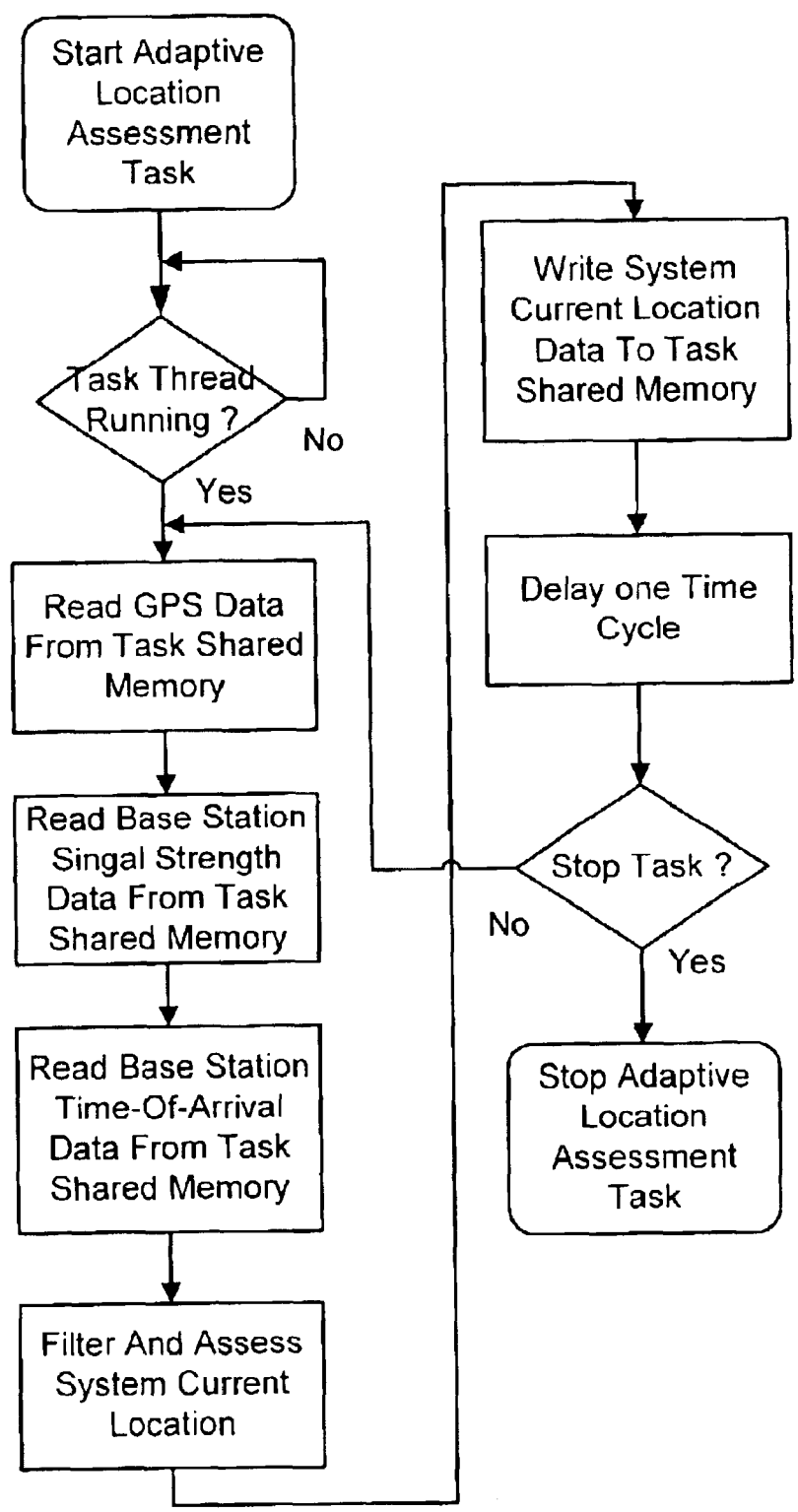
FIG. 23 is a flow chart illustrating the process flow of the Adaptive Location Assessment Task in this invention.
Figure 24:
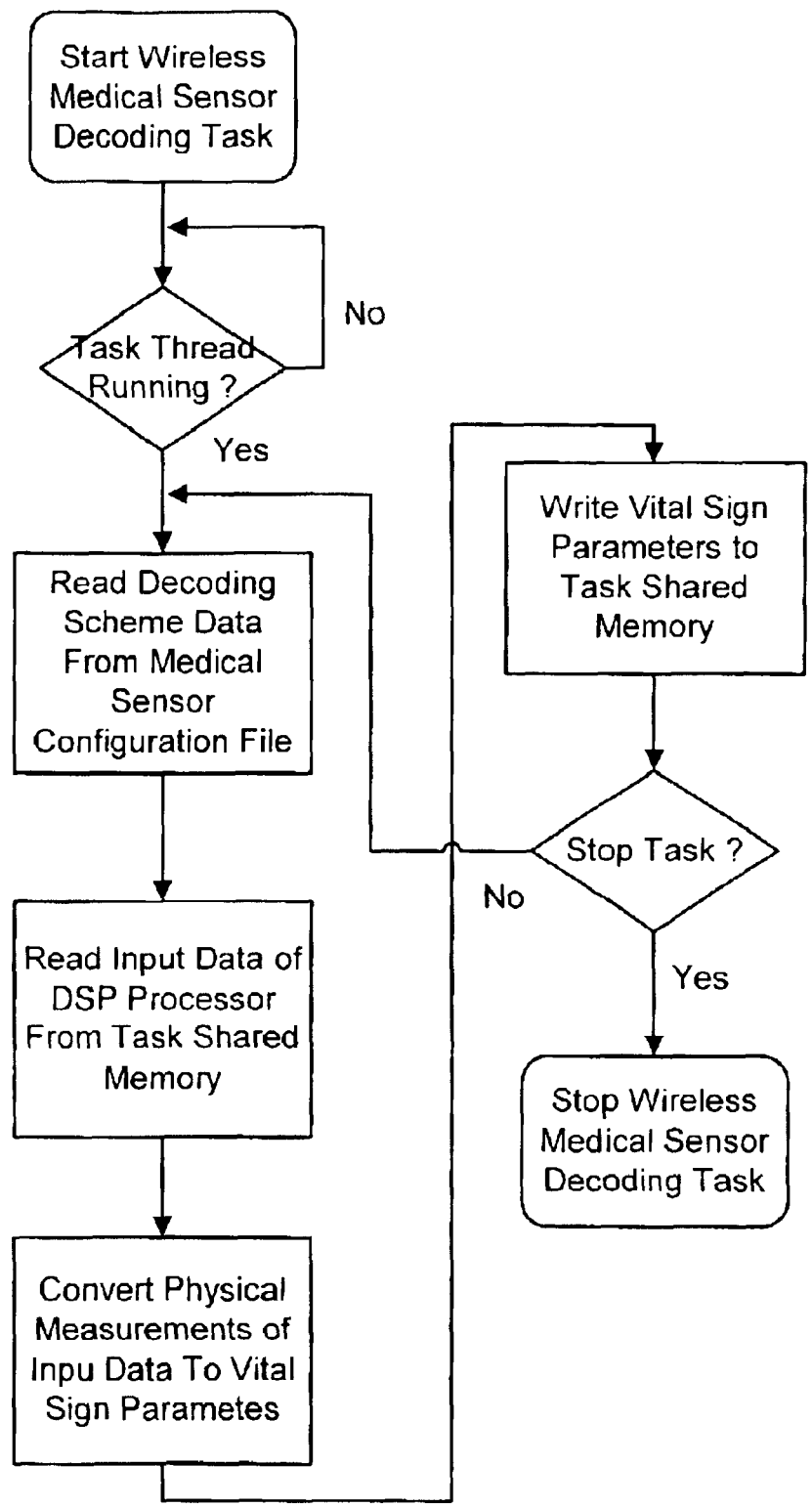
FIG. 24 is a flow chart illustrating the process flow of the Wireless Medical Sensor Decoding Task in this invention.

FIG. 14 is a flow chart illustrating the administration and management process flow of Intelligent Controller 510. FIG. 15 is a flow chart illustrating the process flow of Global Position Data Acquisition Task 520. FIG. 16 is a flow chart illustrating the process flow of Two-Way Wireless Communication Task 521. FIG. 17 is a flow chart illustrating the process flow of Panic Button Task 522. FIG. 18 is a flow chart illustrating the process flow of HTTP Request Processing Task 523. FIG. 19 is a flow chart illustrating the process flow of Patient Vital Sign Processing Task 529. FIG. 20 is a flow chart illustrating the process flow of On/Off Button Task 526. FIG. 21 is a flow chart illustrating the process flow of Alert Beeper Activation Task 527. FIG. 22 is a flow chart illustrating the process flow of Battery Management Task 528. FIG. 23 is a flow chart illustrating the process flow of Adaptive Location Assessment Task 525. FIG. 24 is a flow chart illustrating the process flow of Wireless Medical Sensor Decoding Task 524.

At system startup, Real-Time Operating System (RTOS) is first loaded into System Memory 140. RTOS then loads and starts Intelligent Controller 510. Intelligent Controller 510 first reads configuration data, which includes a set of control rules from Flush Memory 150 and writes the control rules to Task Shared Memory 512. Task Control Administrator 511 of Intelligent Controller 510 then starts the rule engine and uses the control rules to create a plurality of Task Shared Memory 512 to be used by all related tasks. Also using the control rules, Task Control Administrator 511 creates separate parallel execution thread for Global Position Data Acquisition Task 520, Two-Way Wireless Communication Task 521, HTTP Request Processing Task 522, Adaptive Location Assessment Task 525, Panic Button Task 522, On/Off Button Task 526, Alert Beeper Activation Task 527 and Battery Management Task 528. In addition, Task Control Administrator 511 creates separate execution threads for a plurality of Wireless Medical Sensor Decoding Task 524, and Patient Vital Sign Processing Task 529. After the creation of execution threads, Task Control Administrator 511 starts and registers all running tasks at Task Shared Memory 512. Task Control Administrator 511 also publishes those tasks that can be used by other tasks at Task Shared Memory 512. During the task operation, Task Control Administrator 511 can stop or restart a thread for a particular task at the system's request or when triggered by different task conditions. At system shutdown, Task Control Administrator 511 stops all execution threads, and clears all entries at Task Shared Memory 512.

Global Position Data Acquisition Task 520 begins with the initialization of the system clock time. Global Position Data Acquisition Task 520 then starts a new request by initializing a new GPS position and clock time. Each satellite is tracked by Global Position Data Acquisition Task 520 through a different signal channel. After identifying each GPS channel, Global Position Data Acquisition Task 520 first gets the satellite code signal and clock time. Global Position Data Acquisition Task 520 then calculates satellite distance, and posts distance and clock data to Task Shared Memory 512. Once distance and clock time data have been collected for all channels, Global Position Data Acquisition Task 520 calculates GPS position using satellite distance and clock time data. Global Position Acquisition Task 520 proceeds to calculate GPS receiver's velocity and heading. This information is written onto Task Shared Memory 512. If updating the satellite message data is needed, Global Position Data Acquisition Task 520 downloads ephemeredes data from satellites and writes this information onto Task Shared Memory 512. The execution of Global Position Data Acquisition Task 520 continues until it has been terminated by Intelligent Controller 510.

Two-Way Wireless Communication Task 521 processes both incoming and outgoing signals from Long-Range Two-Way Wireless Communication Module 130 which is connected to Multi-Band Long-Range Wireless RF Antenna 200. To process the incoming wireless communication signal, Two-Way Wireless Communication Task 521 first receives the incoming signal from the multiple access channel of Long-Range Two-Way Wireless Communication Module 130, and then writes it to Task Shared Memory 512. To process the outgoing wireless communication signal, Two-Way Wireless Communication Task 521 first reads byte data from Task Shared Memory 512, and then routes it to Long-Range Two-Way Wireless Communication Module 130 to be transmitted through the multiple access channel. The execution of Two-Way Wireless Communication Task 521 continues until it has been terminated by Intelligent Controller 510.

Adaptive Location Assessment Task 525 begins with the checking of GPS location message at Task Shared Memory 512. If there is an up-to-time GPS location message, Adaptive Location Assessment Task 525 reads the GPS data from Task Shared Memory 512 and writes the message of the current GPS location source onto Task Shared Memory 512. If there is no up-to-time GPS message, Adaptive Location Assessment Task 525 writes the message of GPS-not-available onto Task Shared Memory 512. Adaptive Location Assessment Task 525 is then checking Task Shared Memory 512 to see if there is an up-to-time Base Station signal strength message or Time-Of-Arrival message at Task Shared Memory 512. If one exists, Adaptive Location Assessment Task 525 then writes the message of the current Base Station location source onto Task Shared Memory 512. If there is no up-to-time Base Station signal strength message or Time-Of-Arrival message, Adaptive Location Assessment Task 525 writes the message of base-station-not-available onto Task Shared Memory 512. Adaptive Location Assessment Task 525 then uses the information from Task Shared Memory 512, which include the current GPS location source, the current Base Station location source, the previous stored GPS location source, and the previous stored Base Station location source, to filter and assess the current location of the Wireless Communication and Global Location Enabled Intelligent Health Monitoring System. This information is written onto Task Shared Memory 512 to be used by other related application tasks. The execution of Adaptive Location Assessment Task 525 continues until it has been terminated by Intelligent Controller 510.

Panic Button Task 522 begins with the checking of panic button message at Task Shared Memory 512. The panic button message is from System Interface Processor 113 which monitors the button status of Panic Button 170 in real-time. When Panic Button 170 is pressed, System Interface Processor 113 writes a panic button message onto Task Shared Memory 512. This message is read by Panic Button Task 522 which then proceeds to read the patient's current location data and vital sign data at Task Shared Memory 512 to prepare a panic message. The panic message is written onto Task Shared Memory 512 and later is transmitted to a designated location through Two-Way Wireless Communication Task 521. The execution of Panic Button Task 522 continues until it has been terminated by Intelligent Controller 510.

HTTP Request Processing Task 523 begins with the reading HTTP configuration data from Flush Memory 150. HTTP Request Processing Task 523 then starts the HTTP Web Server which contains port listeners and request handlers. Once HTTP Request Processing Task 523 is up and running, it checks the HTTP request message at Task Shared Memory 512. The HTTP request message is from Two-Way Wireless Communication Task 521. If there is a HTTP request at Task Shared Memory 512 waiting to be processed, HTTP Request Processing Task 523 reads the request, and then tries to validate the authorization and authentication of the request specified in the configuration data. After the request has been validated, HTTP Request Processing Task 523 reads data contained in the HTTP request, interrogates the data, and determines what actions must be taken. The action could be reading more data from Task Shared Memory 512 or posting data to Task Shared Memory 512. Permissions to take certain actions by HTTP Request Processing Task 523 are also specified in the HTTP configuration data. HTTP Request Processing Task 523 then writes a returned request message to Task Shared Memory 512. The returned request message is then transferred from Task Shared Memory 512 to Long-Range Two-Way Wireless Communication Module 130 by Two-Way Wireless Communication Task 521. The execution of HTTP Request Processing Task 523 continues until it has been terminated by Intelligent Controller 510.

Patient Vital Sign Processing Task 529 begins by reading the measurement parameters at Task Shared Memory 521 of System Main Memory 140 and re-setting all data entries. Patient Vital Sign Processing Task 529 then checks for a measurement message at Task Shared Memory 512. If there is a measurement message waiting to be processed, Patient Vital Sign Processing Task 524 first reads measurement signals at Task Shared Memory 512, and then filters the measurement signals to match the pre-defined pattern. The results of matched pattern are then written onto Task Shared Memory 512 for use by other related application tasks. Patient Vital Sign Processing Task 529 continues to examine matched pattern against the alert threshold. If an alert is triggered, Patient Vital Sign Processing Task 529 writes an alert message to Task Shared Memory 512. This alert message is later transmitted to a designated location through Two-Way Wireless Communication Task 521. The execution of Patient Vital Sign Processing Task 529 continues until it has been terminated by Intelligent Controller 510.

On/Off Button Task 526 begins by checking the on/off button message at Processor Shared Memory 512. The On/Off button message is from System Interface Processor 113 which monitors the on/off status of On/Off Button 180 in real-time. When On/Off Button 180 is pressed, System Interface Processor 130 writes the on/off button message onto Task Shared Memory 512. This message is then read by On/Off Button Task 522 which checks the current status of On/Off button. If the status of On/Off Button 180 is on, On/Off Button Task 526 writes a sleep mode message to Task Shared Memory 512. This sleep mode message is then read by Task Control Administrator 512 of Intelligent Controller 510, and later puts all task threads into sleep mode. If the status of On/Off Button 180 is off, On/Off Button Task 526 writes a wake-up message onto Task Shared Memory 512. This wake-up message is later read by Task Control Administrator 512 of Intelligent Controller 510 to wake up all task threads. While a task thread is in sleep mode, all temporary stacks and variables remain in System Main Memory 140 and is ready to be used after the task thread is resumed. The execution of Panic Button Task 522 continues until it has been terminated by Intelligent Controller 510.

Alert Beeper Activation Task 527 begins by checking the alert configuration message of Task Shared Memory 512. The alert message is written by Patient Vital Sign Processing Task 529. If there is an alert message at Task Shared Memory 512, Alert Beeper Activation Task 527 sends an activation signal to System Interface Processor 113 which is connected to Alert Beeper 190. The sound and/or vibration of Alert Beeper 190 warns the patient about the critical condition of his/her vital signs. Alert Beeper Activation Task 527 can be configured to send out an alert message for immediate assistance. In this case, Alert Beeper Activation Task 527 reads the current location and vital sign data from Task Shared Memory 512 to prepare an alert message. This alert message is then written onto Task Shared Memory 512 and later is transmitted to a pre-defined location for further action through Two-Way Wireless Communication Task 521. The execution of Alert Beeper Activation Task 527 continues until it has been terminated by Intelligent Controller 510.

Battery Management Task 528 reads battery power level message from Task Shared Memory 512 at a pre-determined time interval. The battery level message is written by System Interface Processor 113 which is connected to Removable/Rechargeable Battery 160. If battery power level is below minimum required level to operate Main Processing Unit Apparatus 100, Battery Management Task 528 reads battery conservation parameters from Task Shared Memory 512. Based on these conservation parameters, Battery Management Task 528 puts low priority tasks in sleep mode by writing a sleep mode message onto Task Shared Memory 512. This sleep mode message is later read by Task Control Administrator 511 to put those tasks in sleep mode. If the battery power level is above minimum required level to operate Main Processing Unit Apparatus 100 and there are tasks that have been put into sleep mode previously, Battery Management Task 528 will wake up those tasks by writing a wake-up message onto Task Shared Memory 512. The wake-up message is later read by Task Control Administrator 511 to wake up those tasks. The execution of Battery Management Task 528 continues until it has been terminated by Intelligent Controller 510.

Adaptive Location Assessment Task 525 starts to acquire GPS location data if GPS satellites are at the line-of-sight of the Wireless Communication and Global Location Enabled Intelligent Health Monitoring System. Adaptive Location Assessment Task 525 then proceeds to measure the strength of a RF signal sent from the Base Station of nearby cellular network tower or to measure the signal's Time-Of-Arrival (TOA) from the Base Station to the Wireless Communication and Global Location Enabled Intelligent Health Monitoring System. The location is then calculated through triangulation of signal strength or signal TOA from the Base Station. Adaptive Location Assessment Task 525 filters and assesses the patient's location based on the availability and accuracy of the GPS data and Base Station distance. The patient's assessed location is written to Task Shared Memory 512 for use by other tasks. The execution of Adaptive Location Assessment Task 525 continues until it has been terminated by Intelligent Controller 510

Wireless Medical Sensor Decoding Task 529 first reads decoding scheme data from the medical sensor configuration file. Wireless Medical Sensor Decoding Task 529 then inputs digital data from DSP Processor 112 and uses decoding scheme data to convert the physical measurements into vital sign parameters. The patient's vital sign parameters are written onto Task Shared Memory 512 for use by other tasks. The execution of Wireless Medical Sensor Decoding Task 529 continues until it has been terminated by Intelligent Controller 510.

CONCLUSIONS, RAMIFICATIONS, AND SCOPE

Accordingly, it can be seen that the Wireless Communication and Global Location Enabled Intelligent Health Monitoring System in this invention provides an active, real-time monitoring method to measure and process the patient's vital signs for providing an alert on location and transmitting an emergency request to a remote patient monitoring station for immediate assistance. The two-way wireless communication and global location data capabilities combined with the adaptive location assessment method notifies an Emergency Service Vehicle to be dispatched to the location of the patient who wears the system under an urgent situation. The system includes a HTTP Web server that can respond to a wireless remote request either from the patient monitoring station or the patient's family members using a standard Internet browser anywhere and anytime. The system uses an intelligent control and a plurality of task shared memory to administrate and manage all related application tasks that are running under separate parallel execution threads. The system also uses a rechargeable/removable battery in conjunction with software that controls the recharging and conservation of the system's power.

Although the description above contains many specificities, these should not be construed as limiting the scope of the invention but as merely providing illustrations for some of the presently preferred embodiments of this invention. Various other embodiments and ramifications are possible within the invention's scope. For example, the Wireless Communication and Global Location Enabled Intelligent Health Monitoring System in this invention can also be used to collect information about the patient's exposure to certain environment while the patient is on the move. In this extended application, an environment measurement device, which can be used to sense and measure environment parameters, such as air composition, air pressure, and temperature, can be used in conjunction with the patient vital sign measurement devices. This type of application is very useful for clinical tests of new drugs and new treatment procedures. Another example would be to use the system in this invention without any patent vital sign measurement devices attached to it. In this alternative application, the system is used as a tracking device for those patients who might have memory problem and cannot remember his/her whereabouts. Another example would be to use the adaptive location assessment method in this invention for other location-based services and applications. Locating vehicle, tracking remote asset, and locating facilities (restaurant, movie theater, merchant store) are some examples of these types of applications.

Thus the scope of this invention should be determined by the appended claims and their legal equivalents, rather than by the examples given.

What is claimed is:

1. A wireless communication and global location enabled intelligent health monitoring system comprising of (A) a plurality of wireless medical sensor apparatus for measuring patient vital signs on different parts of patient body, the said wireless medical sensor apparatus includes (1) an active sensor, and means for detecting physical variables of patient relevant vital signs, (2) a transducer, and means for converting physical measurement into alternative digital form, (3) a digital-to-analog converter, and means for converting digital data from said transducer to analog signal, (4) a frequency synthesis, and means for synthesizing signal frequency at short-range wireless communication bandwidth, (5) a plurality of bandpass filter, and means for band pass filtering signals to desired level, (6) a plurality of linear power amplifier, and means for amplifying signals to desired level, (7) a signal mixer, and means for mixing signals to desired level, (8) a packaged antenna, and means for transmitting short-range radio frequency signals, (9) a thin-film battery, and means for providing power source of said wireless medical sensor apparatus, and (B) a main processing unit apparatus that contains (1) main microcontroller that includes system processor, Digital Signal Processing (DSP) processor, system interface processor, Global Position System (GPS) module and long-range two-way wireless communication module connecting to multi-band long-range wireless Radio Frequency (RF) antenna, short-range RF receiver, system main memory, flash memory, panic button, on/off button, alter beeper and removable/rechargeable battery, and (2) a system software that contains a plurality of task shared memory, and intelligent controller with a task control administrator to manage and control the execration of application tasks, and the said application tasks include global position data acquisition task, two-way wireless communication task, adaptive location assessment task, panic button task, Hypertext Transmission Protocol (HTTP) request processing task, wireless medical sensor decoding task, on/off button task, alert beeper activation task, battery management task, and patient vital sign processing task, and the said intelligent controller uses an active, real-time monitoring method to measure and process vital signs and location information for providing alert on location and transmitting emergency request to remote patient monitoring station for immediate assistance, and the said system software includes a HTTP Web server that can respond to a remote request sent wirelessly either from a patient monitoring station or a patient's family member through a standard Internet browser, anywhere and anytime, and the said intelligent controller and all said application tasks of the said system software are running under separate system threads concurrently to fully utilize system processing power, and the said intelligent health monitoring system uses a rechargeable/removable battery in conjunction with a software control to recharge the system and conserve system power consumption.

2. The main processing unit apparatus as recited in claim 1, comprising:
   (a) a main microcontroller, and means for processing digital signals, interfacing with input/output devices, and conducting system related computations,
   (b) a global position system module, and means for acquiring and processing data from multiple global position system satellites,
   (c) a long-range two-way wireless communication module, and means for receiving and transmitting long-range wireless signals and protocols, and acquiring signal strength and time-of-arrival data from nearby base station cellular towers,
   (d) a short-range radio frequency receiver, and means for receiving short-range wireless signals and protocols from said wireless medical sensor apparatus, and for inputting said short-range wireless signal and protocols to said main microcontroller,
   (e) a system main memory, and means for using as system memory of said main microcontroller, (f) a flash memory, and means for storing data from two-way wireless communication processing, global position processing and related application tasks, (g) a panic button, and means for sending emergency message for immediate assistance at patient request, (h) an on/off button, and means for turning on and off system at patient request, (i) an alert beeper, and means for alerting patient when vital signs exceeding pre-defined threshold, (j) a removable/rechargeable battery, and means for conserving and recharging system battery power.

3. The main microcontroller as recited in (a) of claim 2, comprising:

(a) a system processor, and means for conducting concurrent processing of two-way wireless communication signal, global position system (gps) data acquisition, and related application tasks, (b) a digital signal processing (dsp) processor, and means for processing digital signals from said wireless medical sensor apparatus, (c) a system interface processor, and means for receiving/transmitting signals from said panic button, said on/off button, said alert beeper, and reading/writing data from/to said system main memory and said flush memory.

4. The short-range radio frequency receiver as recited in (d) of claim 2, comprising:

(a) a packaged antenna, and means for receiving short-range radio frequency signals from said wireless medical sensor apparatus, (b) a frequency synthesis, and means for synthesizing signal frequency at short-range wireless communication bandwidth, (c) a plurality of bandpass filter, and means for band pass filtering signals to desired level, (d) a plurality of linear power amplifier, and means for amplifying signals to desired level, (e) a signal mixer, and means for mixing signals at desired level, (f) an analog-to-digital converter, and means for converting analog signals from said wireless medical sensor apparatus to digital data.

5. The long-range wireless signals and protocols as recited in (c) of claim 3, is selected to use global services for mobile (gsm) protocol.

6. The long-range wireless signals and protocols as recited in (c) of claim 2, is selected to use code division multiple access (cdma) protocol.

7. The long-range wireless signals and protocols as recited in (c) of claim 2, is selected to use general packet radio service (gprs) protocol.

8. The long-range wireless signals and protocols as recited in (c) of claim 2, is selected to use cellular digital packet data (cdpd) protocol.

9. The long-range wireless signals and protocols as recited in (c) of claim 2, is selected to use global satellite communication protocol.

10. The short-range wireless signals and protocols as recited in (d) of claim 2, is selected to use bluetooth protocol.

11. The short-range wireless signals and protocols as recited in (d) of claim 2, is selected to use wireless ethernet 802.11 protocol.

12. The system software as recited in claim 1, comprising:

(a) a real-time operating system, and means for executing system start-up, memory configurations, input and output configurations, data file configurations, and system shutdown of said system processor, (b) an intelligent controller, and means for administrating and managing said related application tasks of said system processor.

13. The intelligent controller as recited in (b) of claim 12, comprising:

(a) a task control administrator for administrating and managing said related application tasks, (b) a plurality of task shared memory for storing and manipulating data entries of said related application tasks during system execution.

14. The task control administrator as recited in (a) of claim 13, comprising:

(a) a plurality of control rules, and means for describing control instructions of said related application tasks, (b) a rule engine, and means for executing said control rules.

15. The intelligent controller as recited in (b) of claim 12 administrate and manage of said related application tasks of:

(a) a global position data acquisition task, (b) a two-way wireless communication task, (c) a panic button task, (d) a hypertext transmission protocol (http) request processing task, (e) a patient vital sign processing task, (f) an on/off button task, (g) an alert beep activation task, (h) a battery management task, (i) an adaptive location assessment task, (j) a wireless medical sensor decoding task.

16. The global position data acquisition task as recited in (a) of claim 15, comprising the steps of:

(a) checking system status of said global processing task, (b) initializing system clock time if global position system is up, (c) initializing new request for position and clock time, (d) getting global position system channel, (e) getting satellite code signal and clock time, (f) calculating satellite distance, (g) posting satellite distance and time data to said task shared memory, (h) calculating the position of said global position system with satellite distance and time data if the data from all channels have been acquired, (i) calculating receiver's velocity and heading, (j) writing said global position system and receiver data to said task shared memory, (k) downloading ephemeredes data from satellite if updating satellite message data is needed, (l) repeating steps (c) through (k) while said global position processing task is running, (m) stopping said global position processing task at the request of intelligent controller.

17. The two-way wireless communication task as recited in (b) of claim 15, comprising the steps of:

(a) checking system status of said two-way wireless communication task, (b) receiving incoming signal from multiple access channel, (c) demodulating said income message using configurable demodulation routine, (d) processing line decoding,
(e) processing channel decoding,
(f) processing packet un-framing,
(g) writing byte data to said task shared memory,
(h) repeating steps (b) through (g) while there is an incoming wireless signals,
(i) reading byte data from said task shared memory,
(j) processing packet framing of said byte data,
(k) processing channel coding,
(l) processing line coding,
(m) modulating outgoing signals using configurable modulation routine,
(n) transmitting said outgoing signals to said multiple access channel,
(o) repeating steps (i) through (n) while there is an outgoing wireless signals,
(p) stopping said two-way wireless communication task at the request of said intelligent controller.

18. The panic button task as recited in (c) of claim 15, comprising the steps of:
(a) checking running status of said panic button task,
(b) checking panic button message at said task shared memory,
(c) reading said global position system data from said task shared memory,
(d) preparing panic message with said global position system data and said patient vital sign data,
(e) writing said panic message to said task shared memory,
(f) repeating steps (b) through (e) while there are said panic button messages at said task shared memory, and said panic button task is running,
(g) stopping said panic button task at the request of said task control administrator.

19. The http request processing task as recited in (d) of claim 15, comprising the steps of:
(a) checking running status of said http request processing task,
(b) starting http web server,
(c) checking http request message at said task shared memory,
(d) reading data containing in http request from said task shared memory,
(e) reading data from said task shared memory if additional data is needed,
(f) processing said http request data,
(g) writing returned http request data to said task shared memory if returning http request is needed,
(h) repeating steps (c) through (g) while there are said http request messages at said task shared memory, and said http request task is running,
(i) stopping said http web Server and said http the request task at request of said task control administrator.

20. The patient vital sign processing task as recited in (e) of claim 15, comprising the steps of:
(a) checking running status of said patient vital sign processing task,
(b) reading measurement parameters,
(c) resetting patient vital sign data entry,
(d) checking measuring signal from said task shared memory,
(e) filtering said measurement signal,
(f) detecting said measurement signal,
(g) matching the detected signal with pre-defined pattern,
(h) writing matched pattern to said task shared memory,
(i) examining said matched pattern against an alert threshold,
(j) writing alert message to said task shared memory,
(k) re-reading said measurement parameters and re-setting said patient vital sign data entry if reconfiguration of said measurement parameters are needed,
(l) repeating steps (b) through (k) while there are said measuring message, and said patient vital sign processing task is running,
(m) stopping said patient vital sign processing task at request of said task control administrator.

21. The on/off button task as recited in (f) of claim 15, comprising the steps of:
(a) checking running status of said on/off button task,
(b) checking on/off button message at said task shared memory,
(c) reading on/off status at said task shared memory,
(d) checking status value of said on/off button task,
(e) writing sleeping mode message to said task shared memory if status value is on,
(f) writing walking up message to said task shared memory if status value is off,
(g) repeating steps (b) through (f) while there are said on/off button messages at said task shared memory, and said on/off button task is running,
(h) stopping said on/off button task at the request of said task control administrator.

22. The alert beeper activation task as recited in (g) of claim 15, comprising the steps of:
(a) checking running status of said alert beeper activation task,
(b) calculating said patient vital sign data,
(c) checking said patient vital sign data against alert threshold,
(d) sending activation signal to alert beeper if an alert is triggered,
(e) reading said global position system data and said patient vital sign data from said task shared memory,
(f) preparing alert message with said global position system data and said patient vital sign data,
(g) writing said alert message to said task shared memory,
(h) delaying one time cycle,
(i) repeating steps (b) through (h) while said alert beeper activation task is running,
(j) stopping said alert beeper activation task at the request of said task control administrator.

23. The battery management task as recited in (h) of claim 15, comprising the steps of:
(a) checking running status of said battery management task,
(b) checking system battery power level,
(c) reading battery conservation parameters from said task shared memory if battery power level is below minimum level,
(d) writing sleeping mode message to said task shared memory,
(e) writing low battery message to said task shared memory, (f) checking any tasks in sleeping mode if battery power level is above minimum level, (g) writing walking up message to said task shared memory, (h) delaying one time cycle, (i) repeating steps (b) through (h) while said battery management task is running, (j) stopping said battery management task at the request of said task control administrator.

24. The adaptive location assessment task as recited in (i) of claim 15, comprising the steps of:

(a) checking running status of said adaptive location assessment task, (b) reading gps data from said task shared memory, (c) reading base station signal strength data from said task shared memory, (d) reading base station time-of-arrival data from task shared memory, (e) filtering and assessing system current location, (f) writing said system current location data to said task shared memory, (g) delaying one time cycle, (h) repeating steps (b) through (g) while said adaptive location assessment task is running, (i) stopping said adaptive location assessment task at the request of said task control administrator.

25. The wireless medical sensor decoding task as recited in (j) of claim 15, comprising the steps of:

(a) checking running status of said wireless medical sensor decoding task, (b) reading decoding scheme data from medical sensor configuration file, (c) reading input data of said dsp processor from said task sharing memory, (d) converting physical measurements of said input data to vital sign parameters, (e) writing said vital sign parameters onto said task shared memory, (f) repeating steps (c) through (e) while said wireless medical sensor decoding task is running, (g) stopping said wireless medical sensor decoding task at the request of said task control administrator.

26. The intelligent controller as recited in (b) of claim 12, wherein said administrating and managing of said related application tasks, comprising the steps of:

(a) reading intelligent controller configuration and control rule data from said flush memory, (b) starting rule engine, (c) creating said task shared memory, (d) checking running status of all tasks, (e) reading task configuration data of a task if said task needs to be started, (f) creating a task thread for said task, (g) publishing data sharing option to said task shared memory of said task, (h) setting said task running, (i) updating data entry at said task shared memory of said task, (j) writing event notification to said task shared memory of said task, (k) repeating steps (d) through (j) while there are more tasks to be started, (l) stopping said task at the request of said task control administrator, (m) terminating all related application tasks, and clearing said task shared memory at the shutdown request of said task control administrator.

* * * * *